US012783203B2

(12) United States Patent
Kaneko et al.

(10) Patent No.: US 12,783,203 B2
(45) Date of Patent: Nov. 3, 2026

(54) INFORMATION PROCESSING SYSTEM, INFORMATION PROCESSING METHOD, AND INFORMATION PROCESSING PROGRAM

(71) Applicant: FUJIFILM CORPORATION, Tokyo (JP)

(72) Inventors: Yasuhisa Kaneko, Tokyo (JP); Kenji Nagamiya, Tokyo (JP); Tomohide Hiragami, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 185 days.

(21) Appl. No.: 18/809,355

(22) Filed: Aug. 20, 2024

(65) Prior Publication Data

US 2025/0077161 A1 Mar. 6, 2025

(30) Foreign Application Priority Data

Sep. 1, 2023 (JP) ................................ 2023-142511

(51) Int. Cl.

| | |
|---|---|
| ***G06F 3/14*** | (2006.01) |
| ***A61B 1/00*** | (2006.01) |
| ***G06T 11/00*** | (2026.01) |
| ***G09B 9/00*** | (2006.01) |
| ***G09B 23/28*** | (2006.01) |

(52) U.S. Cl.

CPC .......... *G06F 3/1454* (2013.01); *A61B 1/0005* (2013.01); *G06T 11/00* (2013.01); *G06T 2210/41* (2013.01); *G06T 2210/62* (2013.01); *G09B 9/00* (2013.01); *G09B 23/285* (2013.01)

(58) Field of Classification Search

CPC ..... G06F 3/1454; A61B 1/0005; A61B 1/018; A61B 1/05; A61B 1/000094; A61B 1/045; A61B 1/0638; A61B 1/0655; A61B 1/0669; G06T 11/00; G06T 2210/41; G06T 2210/62; G09B 9/00; G09B 23/285

See application file for complete search history.

(56) References Cited

U.S. PATENT DOCUMENTS

| | | | | |
|---|---|---|---|---|
| 12,594,125 | B2 * | 4/2026 | Palushi | A61B 34/20 |
| 2022/0343586 | A1 * | 10/2022 | Vetter | G06T 15/00 |
| 2023/0281897 | A1 * | 9/2023 | Ishikawa | G06F 3/01<br>345/633 |

FOREIGN PATENT DOCUMENTS

| | | | | |
|---|---|---|---|---|
| JP | 2020-144233 | A | 9/2020 | |
| WO | WO-2024176154 | A2 * | 8/2024 | H04N 13/239 |

* cited by examiner

*Primary Examiner* — Said Broome
*Assistant Examiner* — Jordan Wan Yick
(74) *Attorney, Agent, or Firm* — SOLARIS Intellectual Property Group, PLLC

(57) ABSTRACT

An information processing system including at least one processor, wherein the processor is configured to: acquire a first visual field image showing a visual field of a first user and a second visual field image showing a visual field of a second user; perform control of causing a second display device viewed by the second user to display first interest information indicating a position of at least one first region of interest included in the first visual field image; and perform control of causing a first display device viewed by the first user to display second interest information indicating a position of at least one second region of interest included in the second visual field image.

19 Claims, 14 Drawing Sheets

INFORMATION PROCESSING SYSTEM, INFORMATION PROCESSING METHOD, AND INFORMATION PROCESSING PROGRAM

CROSS-REFERENCE TO RELATED APPLICATIONS

This application claims priority from Japanese Application No. 2023-142511, filed on Sep. 1, 2023, the entire disclosure of which is incorporated herein by reference.

BACKGROUND

Technical Field

The technique of the present disclosure relates to an information processing system, an information processing method, and an information processing program.

Related Art

In the related art, a method is known in which a display device, such as an augmented reality (AR) device, which allows a user to visually recognize a real space and a display image, is applied to a training system for a user to learn an operation. For example, JP2020-144233A discloses that a reference motion picture is displayed on a visual field video of a learner in a superimposed manner on a glasses-type device worn by the learner in order to learn an operation of a probe of an ultrasound imaging apparatus. Further, a display content of the reference motion picture is disclosed to be dynamically changed according to characteristics of a learner's work operation included in the visual field video of the learner.

In recent years, there has been a demand for a technique capable of supporting a teacher to guide a student in real time in order to perform more advanced training according to a work procedure, an instrument to be used, an object, a situation, a degree of proficiency of a student user, and the like. For example, there has been a demand for a technique that allows, in a case where the teacher and the student each perform the same operation in parallel, the student to imitate the teacher's operation or the teacher to give advice on the student's operation.

SUMMARY

The present disclosure provides an information processing system, an information processing method, and an information processing program capable of performing appropriate training.

According to a first aspect of the present disclosure, there is provided an information processing system comprising at least one processor, in which the processor is configured to acquire a first visual field image showing a visual field of a first user and a second visual field image showing a visual field of a second user, perform control of causing a second display device viewed by the second user to display first interest information indicating a position of at least one first region of interest included in the first visual field image, and perform control of causing a first display device viewed by the first user to display second interest information indicating a position of at least one second region of interest included in the second visual field image.

In the above aspect, the processor may be configured to perform control of causing the second display device to display, as the first interest information, an image in which the first visual field image is made to be semi-transparent.

In the above aspect, the processor may be configured to extract the at least one first region of interest from the first visual field image, and perform control of causing the second display device to display, as the first interest information, information indicating a contour of the extracted at least one first region of interest.

In the above aspect, the processor may be configured to extract the at least one first region of interest from the first visual field image, extract the at least one second region of interest from the second visual field image, associate the first region of interest and the second region of interest of the same type with each other, determine whether or not positions of the associated first and second regions of interest are different from each other, and perform control of causing, in a case where the determination is affirmative, the second display device to display, as the first interest information, information indicating a difference between the positions of the associated first and second regions of interest.

In the above form, the processor may be configured to perform control of causing, in a case where the determination is negative, the second display device to display, as the first interest information, the information indicating the difference between the positions of the associated first and second regions of interest in a display form different from the case where the determination is affirmative.

In the above aspect, the processor may be configured to acquire the first visual field image and the second visual field image over time, derive, as a correction value, the difference between the positions of the associated first and second regions of interest, which are extracted respectively from the first visual field image and the second visual field image at an initial point in time, and perform the determination based on a difference obtained by correcting, using the correction value, the difference between the positions of the associated first and second regions of interest, which are extracted respectively from the first visual field image and the second visual field image at a point in time later than the initial point in time.

In the above aspect, the processor may be configured to perform control of displaying, as the first interest information, an image on a left side among images obtained by dividing the first visual field image into two parts of left and right on a left side of a region in which the visual field of the second user is displayed on the second display device, and perform control of displaying, as the first interest information, an image on a right side among the images obtained by dividing the first visual field image into two parts of left and right on a right side of the region in which the visual field of the second user is displayed on the second display device.

In the aspect, the processor may be configured to acquire the first visual field image over time, determine whether or not there is a change in a position or an orientation of the first region of interest from the first visual field image acquired over time, and perform control of causing, in a case where the determination is affirmative, the second display device to display information indicating that there is the change in the position or the orientation of the first region of interest.

In the above aspect, the processor may be configured to acquire first visual line information of the first user, and perform control of causing the second display device to display the first visual line information of the first user.

In the above aspect, the processor may be configured to acquire second visual line information of the second user, specify, based on the second visual line information, a region of interest to be paid attention that is the second region of interest to which the second user pays attention in the second visual field image, acquire, in a case where the region of interest to be paid attention is a predetermined type of region of interest, relevant information related to the region of interest to be paid attention, and perform control of causing the second display device to display the relevant information on the region of interest to be paid attention in a superimposed manner.

In the above aspect, the processor may be configured to acquire a first posture image and a second posture image obtained by respectively imaging the first user and the second user in at least one same direction, and perform control of displaying the first posture image and the second posture image on an outside of a region in which the visual field of the second user is displayed on the second display device.

In the above aspect, the processor may be configured to acquire a voice of the first user, convert the voice of the first user into text information, and perform control of causing the second display device to display the text information.

In the above aspect, the processor may be configured to generate a second composite image obtained by combining the second visual field image with the information indicating the position of the first region of interest, generate a first composite image obtained by combining the first visual field image with the information indicating the position of the second region of interest, perform control of causing the second display device to display the second composite image, and perform control of causing the first display device to display the first composite image.

In the above aspect, the first visual field image and the second visual field image may indicate the visual fields of the first user and the second user in a case where the first user and the second user operate the same type of instrument, and each of the first region of interest and the second region of interest may be at least one of a portion of a body of the first user or the second user who operates the instrument, at least a part of the instrument, a use target of the instrument, or an edge of the first visual field image or the second visual field image.

In the above aspect, the processor may be configured to acquire parameter information related to the instrument, and perform control of causing the second display device to display the parameter information.

In the above aspect, the processor may be configured to perform control of causing a third display device viewed by a third user to display the first interest information.

In the above aspect, the processor may be configured to acquire a first sub-visual field image showing a visual field of a first sub-user and a second sub-visual field image showing a visual field of a second sub-user, perform control of causing a second sub-display device viewed by the second sub-user to display information indicating a position of a first sub-region of interest included in the first sub-visual field image, and perform control of causing a first sub-display device viewed by the first sub-user to display information indicating a position of a second sub-region of interest included in the second sub-visual field image.

In the above aspect, the processor may be configured to acquire a second sub-visual field image showing a visual field of a second sub-user, and perform control of causing the second display device to display the first interest information and information indicating a position of a second sub-region of interest included in the second sub-visual field image.

According to a second aspect of the present disclosure, there is provided an information processing method executed by a computer comprising acquiring a first visual field image showing a visual field of a first user and a second visual field image showing a visual field of a second user, performing control of causing a second display device viewed by the second user to display first interest information indicating a position of at least one first region of interest included in the first visual field image, and performing control of causing a first display device viewed by the first user to display second interest information indicating a position of at least one second region of interest included in the second visual field image.

According to a third aspect of the present disclosure, there is provided an information processing program causing a computer to execute a process comprising acquiring a first visual field image showing a visual field of a first user and a second visual field image showing a visual field of a second user, performing control of causing a second display device viewed by the second user to display first interest information indicating a position of at least one first region of interest included in the first visual field image, and performing control of causing a first display device viewed by the first user to display second interest information indicating a position of at least one second region of interest included in the second visual field image.

According to the above aspect, it is possible to perform the appropriate training with the information processing system, the information processing method, and the information processing program of the present disclosure.

DETAILED DESCRIPTION

Hereinafter, an embodiment of the present disclosure will be described with reference to accompanying drawings.

First, an endoscope system 10 to which the technique of the present disclosure can be applied will be described with reference to FIGS. 1 and 2. The endoscope system 10 is used by a doctor 12 in endoscopy and the like. The endoscopy is assisted by a staff such as a nurse 14.

Figure 1:
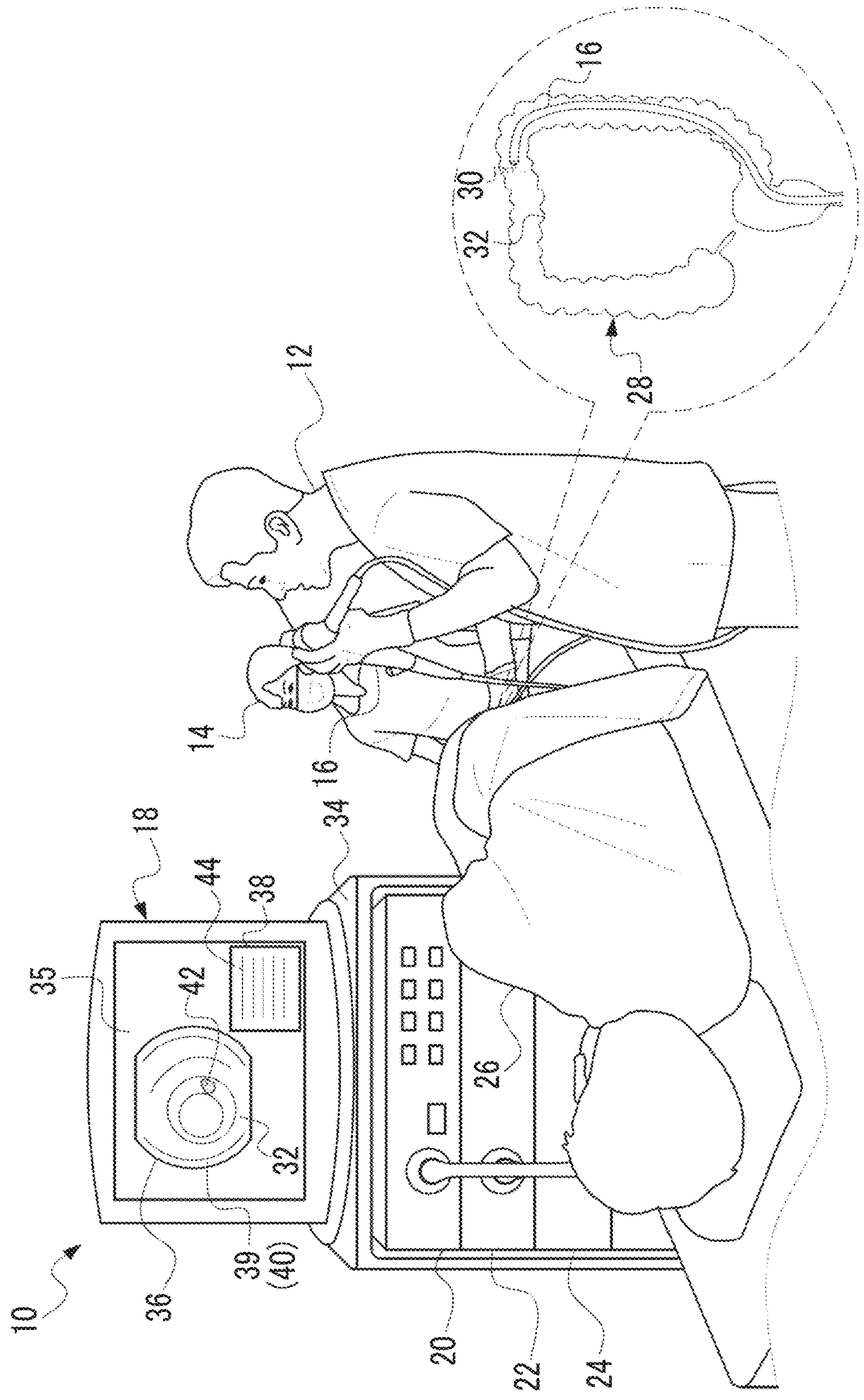
FIG. 1 is a schematic diagram showing an example of an overall configuration of an endoscope system.

As shown in FIG. 1, an endoscope system 10 comprises an endoscope 16, a display device 18, a light source device 20, a control device 22, and an image processing device 24. The light source device 20, the control device 22, and the image processing device 24 are installed in a wagon 34. A plurality of tables are provided in the wagon 34 along a vertical direction, and the image processing device 24, the control device 22, and the light source device 20 are installed from a lower table to an upper table. Further, the display device 18 is installed on an uppermost table in the wagon 34.

The endoscope system 10 is a modality for performing medical treatment on the inside of a body of a subject 26 (for example, a patient) using the endoscope 16. The endoscope 16 is used by the doctor 12 and is inserted into a body cavity (for example, luminal organs such as large intestine, stomach, duodenum, and trachea) of the subject 26. The endoscope system 10 causes the endoscope 16 inserted into the body cavity of the subject 26 to image the inside of the body cavity of the subject 26 and performs various medical treatments in the body cavity as necessary.

For example, in the present embodiment, the endoscope 16 is inserted into a large intestine 28 of the subject 26. The endoscope system 10 images the inside of the large intestine 28 of the subject 26 to acquire and output an image showing an aspect inside the large intestine 28. In the present embodiment, the endoscope system 10 has an optical imaging function of emitting light 30 in the large intestine 28 to image reflected light obtained by being reflected by an intestinal wall 32 of the large intestine 28.

The control device 22 controls the entire endoscope system 10. The image processing device 24 performs various types of image processing on the image obtained by imaging the intestinal wall 32 with the endoscope 16 under the control of the control device 22.

The display device 18 displays various types of information including the image. Examples of the display device 18 include a liquid crystal display and an organic electroluminescence (EL) display. Further, a smartphone, a tablet terminal, or the like may be used instead of or in addition to the display device 18.

A screen 35 is displayed on the display device 18. The screen 35 includes a plurality of display regions. The plurality of display regions are disposed side by side on the screen 35. In the example shown in FIG. 1, a first display region 36 and a second display region 38 are shown as an example of the plurality of display regions. The first display region 36 is used as a main display region, and the second display region 38 is used as a sub-display region.

An endoscopic video image 39 is displayed in the first display region 36. The endoscopic video image 39 is a video image acquired by imaging the intestinal wall 32 in the large intestine 28 of the subject 26 with the endoscope 16. The example shown in FIG. 1 shows a video image in which the intestinal wall 32 appears, as an example of the endoscopic video image 39.

In the example in FIG. 1, the intestinal wall 32 appearing in the endoscopic video image 39 includes a lesion 42 as an observation target region gazed by the doctor 12. The doctor 12 can visually recognize the aspect of the intestinal wall 32 including the lesion 42 through the endoscopic video image 39. Examples of the lesion 42 include a tumor-like polyp and a non-tumor-like polyp.

The image displayed in the first display region 36 is one frame 40, which is included in the video image configured by including a plurality of frames 40 in time series. That is, the plurality of frames 40 in time series are displayed at a predetermined frame rate (for example, several tens of frames/second) in the first display region 36.

Medical information 44, which is information related to medical treatment, is displayed in the second display region 38. Examples of the medical information 44 include information for assisting medical determination or the like by the doctor 12. Examples of such information include various types of information related to the subject 26 and information obtained by performing image analysis using a computer aided diagnosis/detection (CAD) technique on the endoscopic video image 39.

Figure 2:
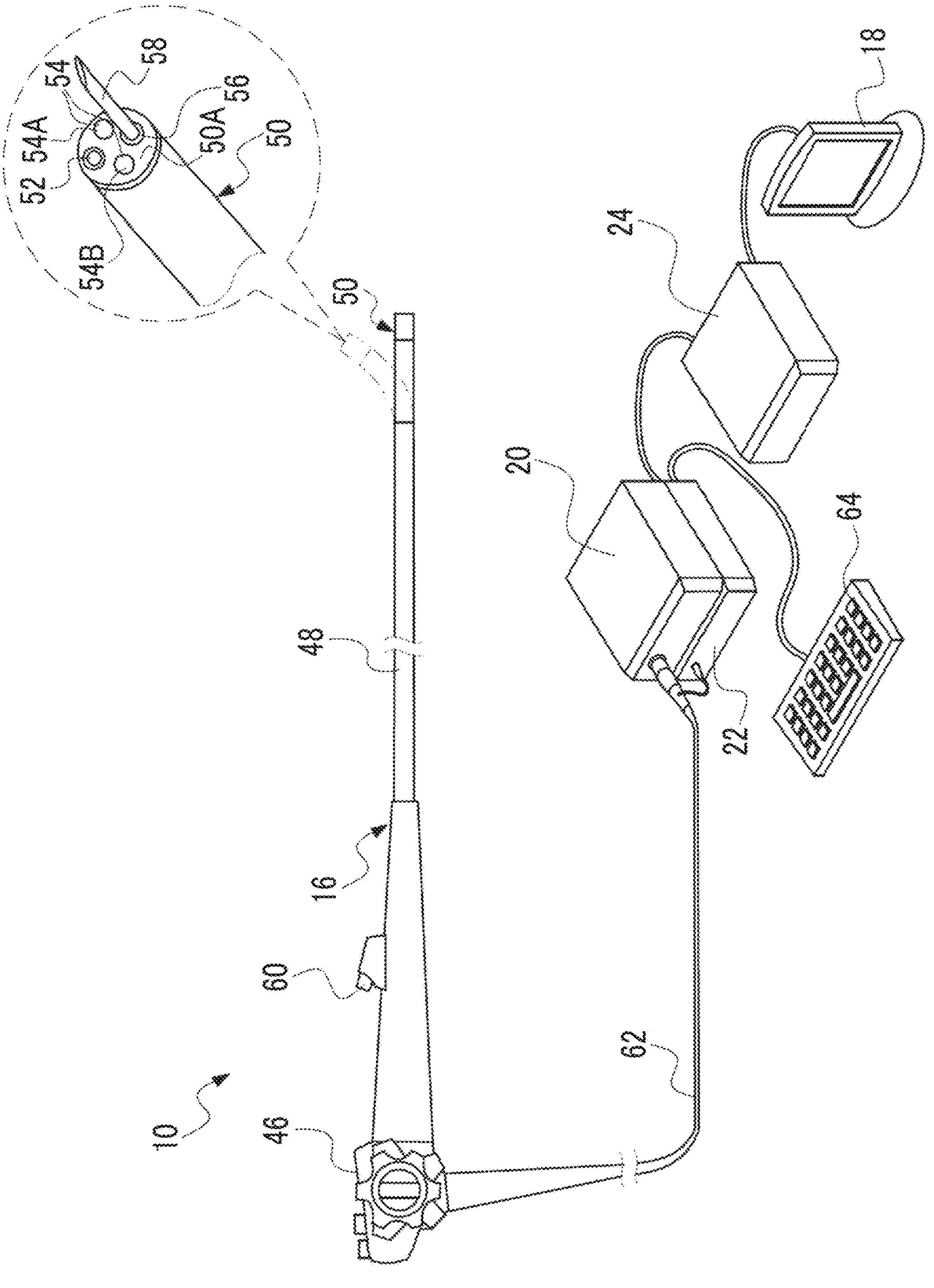
FIG. 2 is a schematic diagram showing an example of the overall configuration of the endoscope system.

As shown in FIG. 2, the endoscope 16 comprises an operation part 46 and an insertion part 48. The insertion part 48 is partially curved by the operation of the operation part 46. The insertion part 48 is inserted into the large intestine 28 while being bent in accordance with a shape of the large intestine 28 in response to the operation of the operation part 46 by the doctor 12.

A tip part 50 of the insertion part 48 is provided with a camera 52, an illumination device 54, and an opening for treatment tool 56. The camera 52 and the illumination device 54 are provided on a distal end surface 50A of the tip part 50. Here, although the form example has been described in which the camera 52 and the illumination device 54 are provided on the distal end surface 50A of the tip part 50, the present disclosure is not limited thereto. The camera 52 and the illumination device 54 may be provided on a side surface of the tip part 50, and thus the endoscope 16 may be configured as a side-viewing endoscope.

The camera 52 is inserted into the body cavity of the subject 26 to image the observation target region. In the present embodiment, the camera 52 images the inside of the body of the subject 26 (for example, the inside of the large intestine 28) to acquire the endoscopic video image 39. Examples of the camera 52 include a complementary metal oxide semiconductor (CMOS) camera and a charge coupled device (CCD) camera.

The illumination device 54 has illumination windows 54A and 54B. The illumination device 54 emits the light 30 via the illumination windows 54A and 54B. Examples of a type of the light 30 emitted from the illumination device 54 include visible light (for example, white light) and invisible light (for example, near-infrared light). Further, the illumination device 54 emits special light via the illumination windows 54A and 54B. Examples of the special light include light for blue light imaging (BLI) and light for linked color imaging (LCI). The camera 52 images the inside of the large intestine 28 by an optical method in a state where the illumination device 54 emits the light 30 in the large intestine 28.

The opening for treatment tool 56 is an opening through which a treatment tool 58 protrudes from the tip part 50. Further, the opening for treatment tool 56 is also used as a suction port that sucks blood, a body waste, and the like, and as a discharge port that discharges a fluid.

A treatment tool insertion port 60 is formed in the operation part 46, and the treatment tool 58 is inserted into the insertion part 48 from the treatment tool insertion port 60. The treatment tool 58 passes through the insertion part 48 and protrudes from the opening for treatment tool 56 to the outside. The example shown in FIG. 2 shows an aspect in which a puncture needle protrudes from the opening for treatment tool 56, as the treatment tool 58. The treatment tool 58 is not limited to the puncture needle, and may be, for example, a grasping forceps, a papillotomy knife, a snare, a catheter, a guide wire, a cannula, or a puncture needle with a guide sheath.

The endoscope 16 is connected to the light source device 20 and the control device 22 via a universal cord 62. The image processing device 24 and a reception device 64 are connected to the control device 22. Further, the display device 18 is connected to the image processing device 24. That is, the control device 22 is connected to the display device 18 via the image processing device 24.

The reception device 64 receives an instruction from the doctor 12 and outputs the received instruction as an electric signal to the control device 22. Examples of the reception device 64 include a keyboard, a mouse, a touch panel, a foot switch, a microphone, and a remote control device.

The control device 22 controls the light source device 20, exchanges various signals with the camera 52, or exchanges various signals with the image processing device 24.

The light source device 20 emits light under the control of the control device 22 and supplies the light to the illumination device 54. The illumination device 54 has a built-in light guide, and the light supplied from the light source device 20 is emitted from the illumination windows 54A and 54B through the light guide. The control device 22 causes the camera 52 to perform imaging, acquires the endoscopic video image 39 from the camera 52, and outputs the endoscopic video image 39 to a predetermined output destination (for example, the image processing device 24).

The image processing device 24 performs various types of image processing on the endoscopic video image 39 input from the control device 22 to support the endoscopy. The image processing device 24 outputs the endoscopic video image 39 subjected to various types of image processing to a predetermined output destination (for example, the display device 18 and the control device 22).

Here, since the image processing device 24 is exemplified as an external device for extending the function performed by the control device 22, the form example is exemplified in which the control device 22 and the display device 18 are indirectly connected via the image processing device 24, but the present disclosure is not limited thereto. For example, the display device 18 may be directly connected to the control device 22. In this case, for example, the control device 22 may be provided with the function of the image processing device 24, or the control device 22 may be provided with a function of executing the same processing as the processing executed by the image processing device 24 on a server (not illustrated) and receiving and using a processing result by the server.

Further, the endoscope system 10 is communicably connected to an information processing apparatus 300 and another external device (not illustrated). Examples of the external device include a server and/or a client terminal (for example, a personal computer, a smartphone, and a tablet terminal) that manage various types of information such as an electronic medical record. The external device receives the information transmitted from the endoscope system 10 and executes processing using the received information (for example, processing of storing the information in the electronic medical record or the like).

However, it is known that it is difficult to learn the operation of the endoscope 16, such as holding method, direction, and force applying method, in the endoscope system 10. For example, as shown in FIG. 1, the doctor 12 operates the operation part 46 with a left hand and operates the insertion part 48 with a right hand while viewing the display device 18 such that the tip part 50 of the endoscope 16 reaches a desired observation target region. In particular, in a case where the large intestine 28 is to be examined, since there is a large individual difference in the movement of the large intestine 28, it is necessary to flexibly change the operation in accordance with the state of the subject 26 (for example, a calm state, a distressed state, or the like).

In a training system 100 of the present disclosure, in a case where a user as a teacher and a user as a student each perform the same operation in parallel, the teacher user and the student user can check the operations of each other. Accordingly, the student can imitate the operation of the teacher, or the teacher can give advice on the operation of the student.

Figure 3:
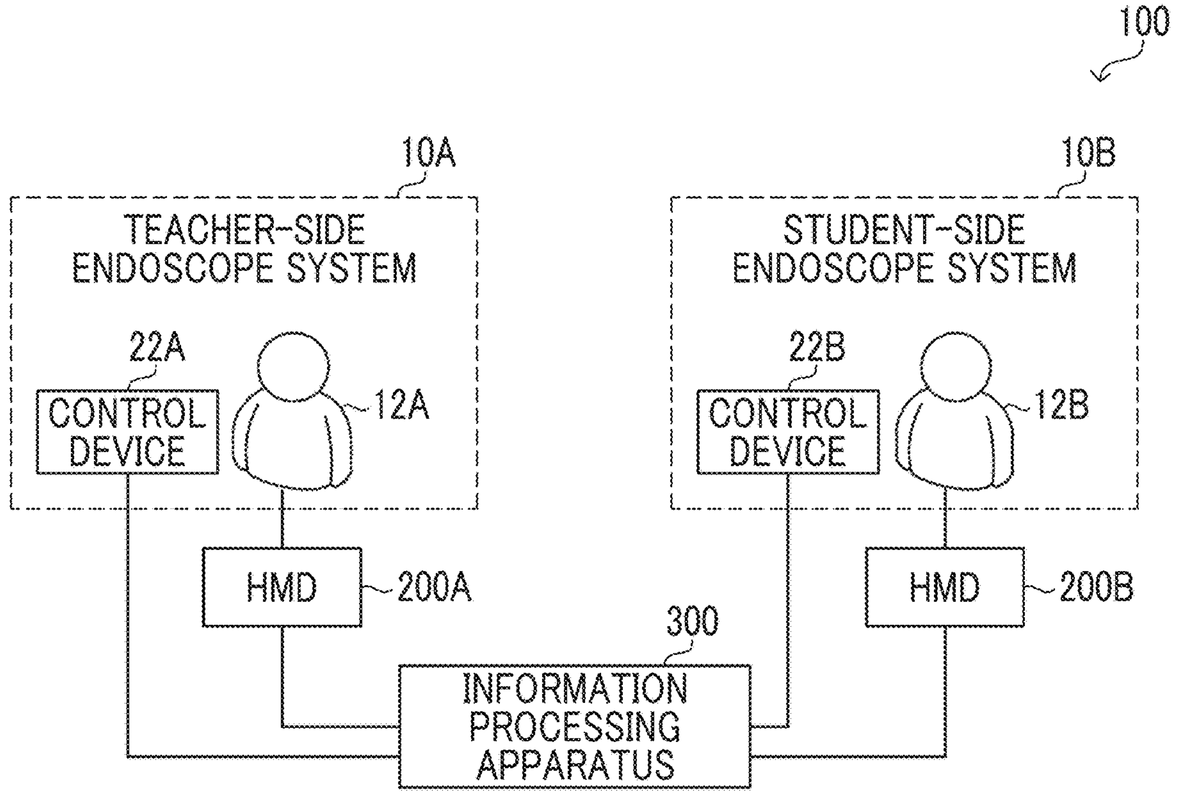
FIG. 3 is a schematic diagram showing an example of an overall configuration of a training system.

The training system 100 of the present disclosure will be described with reference to FIG. 3. In the present embodiment, the training system 100 includes two endoscope systems 10 used by each of the doctor 12 as the teacher (hereinafter referred to as "teacher 12A") and the doctor 12 as the student (hereinafter referred to as "student 12B"). The two endoscope systems 10 may be constructed in the same facility or may be constructed in remote places.

Hereinafter, the endoscope system 10 used by the teacher 12A will be referred to as a "teacher-side endoscope system 10A", and the endoscope system 10 used by the student 12B will be referred to as a "student-side endoscope system 10B". Further, in the following description, in a case where a configuration included in the teacher-side endoscope system 10A is distinguished from a configuration included in the student-side endoscope system 10B, "A" and "B" are added to an end of reference numerals, respectively. The teacher 12A is an example of a first user of the present disclosure, and the student 12B is an example of a second user of the present disclosure.

Subjects 26A and 26B used in the training system 100 may be human bodies, but are preferably models for training (phantoms). This is because the student 12B imitates the operation of the teacher 12A to perform the training in the present training system 100 and thus conditions for the subjects 26A and 26B are preferably the same.

In the training system 100, the teacher 12A and the student 12B each wear a head mounted display (HMD) 200 as an example of a display device viewed by each of the teacher 12A and the student 12B.

Figure 4:
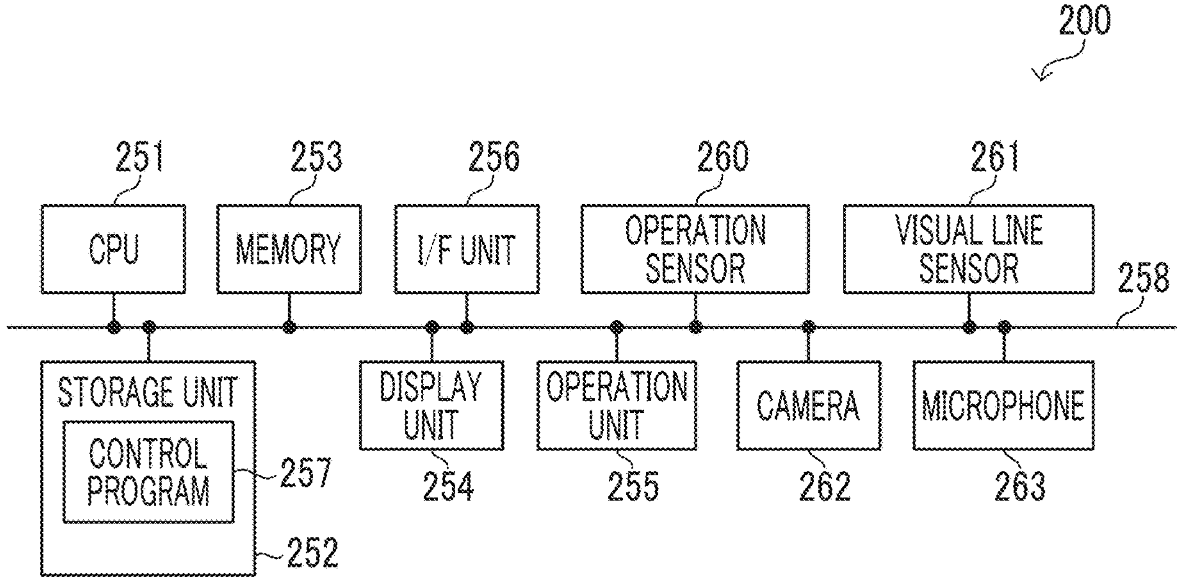
FIG. 4 is a block diagram showing an example of a hardware configuration of an HMD.

An example of a hardware configuration of the HMD 200 will be described with reference to FIG. 4. As shown in FIG. 4, the HMD 200 includes a central processing unit (CPU) 251, a non-volatile storage unit 252, and a memory 253 as a temporary storage region. Further, the HMD 200 includes a display unit 254, an operation unit 255 such as a touch panel, and an interface (I/F) unit 256. Further, the HMD 200 includes an operation sensor 260 that detects an operation of a user to whom the HMD 200 is mounted, a visual line sensor 261 that detects a visual line, a camera 262, and a microphone 263.

The storage unit 252 is formed by, for example, a storage medium such as a flash memory. The storage unit 252 stores a control program 257 that controls the entire HMD 200. The CPU 251 reads out the control program 257 from the storage unit 252, develops the control program 257 into the memory 253, and executes the developed control program 257.

The display unit 254 is configured such that the user wearing the HMD 200 can visually recognize an image (virtual image). For example, the display unit 254 may use a transmissive or non-transmissive display, or may project a video to a retina of the user. The I/F unit 256 performs wired or wireless communication with the information processing apparatus 300, another external device, and the like.

The operation sensor 260 is a sensor that detects the operation of the user wearing the HMD 200, and is, for example, an acceleration sensor, a gyro sensor, a geomagnetic sensor, or the like. The visual line sensor 261 is a sensor that detects where a gaze point of the user wearing the HMD 200 is. The camera 262 is a camera that images a real space observed by the user wearing the HMD 200, and is, for example, a digital camera such as a CMOS camera. The microphone 263 collects a voice and an ambient sound of the user wearing the HMD 200.

The CPU 251, the storage unit 252, the memory 253, the display unit 254, the operation unit 255, the I/F unit 256, the operation sensor 260, the visual line sensor 261, the camera 262, and the microphone 263 are connected to be able to mutually exchange various types of information via a bus 258, such as a system bus and a control bus.

Hereinafter, in a case where the HMD 200 mounted on the teacher 12A is distinguished from the HMD 200 mounted on the student 12B, the HMD 200 mounted on the teacher 12A and the HMD 200 mounted on the student 12B are referred to as "HMD 200A" and "HMD 200B", respectively. Further, in the following description, in a case where a configuration of the HMD 200A is distinguished from a configuration of the HMD 200B, "A" and "B" are added to an end of reference numerals, respectively. The HMD 200A is an example of a first display device viewed by the first user of the present disclosure, and the HMD 200B is an example of a second display device viewed by the second user of the present disclosure.

Further, the training system 100 comprises the information processing apparatus 300. The information processing apparatus 300 is configured to be connectable, via a wired or wireless network, to a control device 22A and the HMD 200A of the teacher-side endoscope system 10A, and a control device 22B and the HMD 200B of the student-side endoscope system 10B, respectively. The training system 100 is an example of an information processing system according to the present disclosure.

Figure 5:
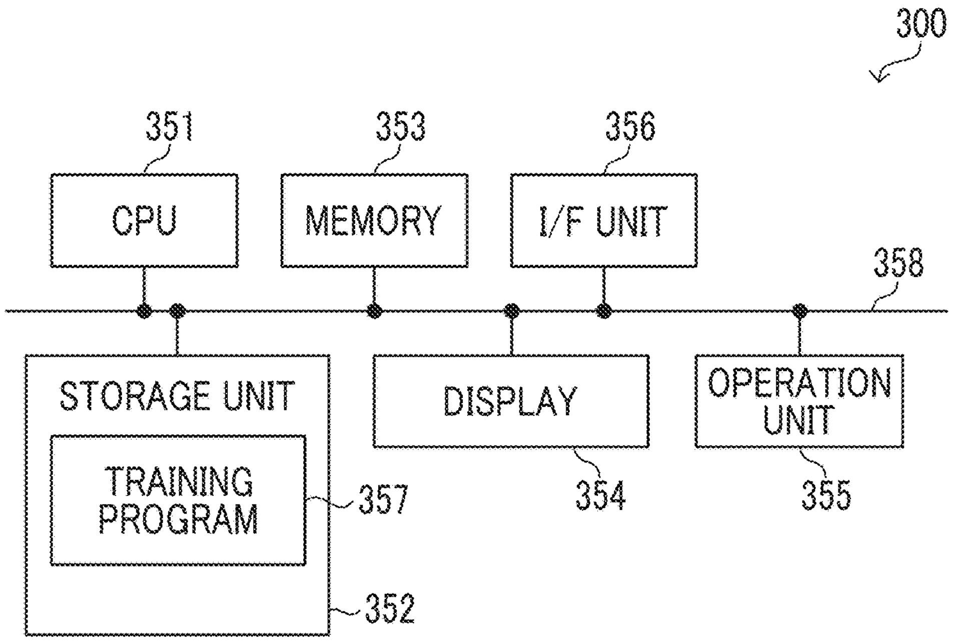
FIG. 5 is a block diagram showing an example of a hardware configuration of an information processing apparatus.

An example of a hardware configuration of the information processing apparatus 300 will be described with reference to FIG. 5. As shown in FIG. 5, the information processing apparatus 300 includes a CPU 351, a non-volatile storage unit 352, and a memory 353 as a temporary storage region. Further, the information processing apparatus 300 includes a display 354, such as a liquid crystal display, an operation unit 355, such as a touch panel, a keyboard, and a mouse, and an I/F unit 356. The I/F unit 356 performs wired or wireless communication with the control device 22A, the control device 22B, the HMD 200A, the HMD 200B, another external device, and the like.

The storage unit 352 is formed by a storage medium such as a hard disk drive (HDD), a solid state drive (SSD), and a flash memory. The storage unit 352 stores a training program 357 in the information processing apparatus 300. The CPU 351 reads out the training program 357 from the storage unit 352, develops the training program 357 into the memory 353, and executes the developed training program 357. The training program 357 is an example of an information processing program according to the present disclosure.

The CPU 351, the storage unit 352, the memory 353, the display 354, the operation unit 355, and the I/F unit 356 are connected to be able to mutually exchange various types of information via a bus 358, such as a system bus and a control bus. As the information processing apparatus 300, for example, a personal computer, a server computer, a smartphone, a tablet terminal, a wearable terminal, or the like can be applied as appropriate.

Figure 6:
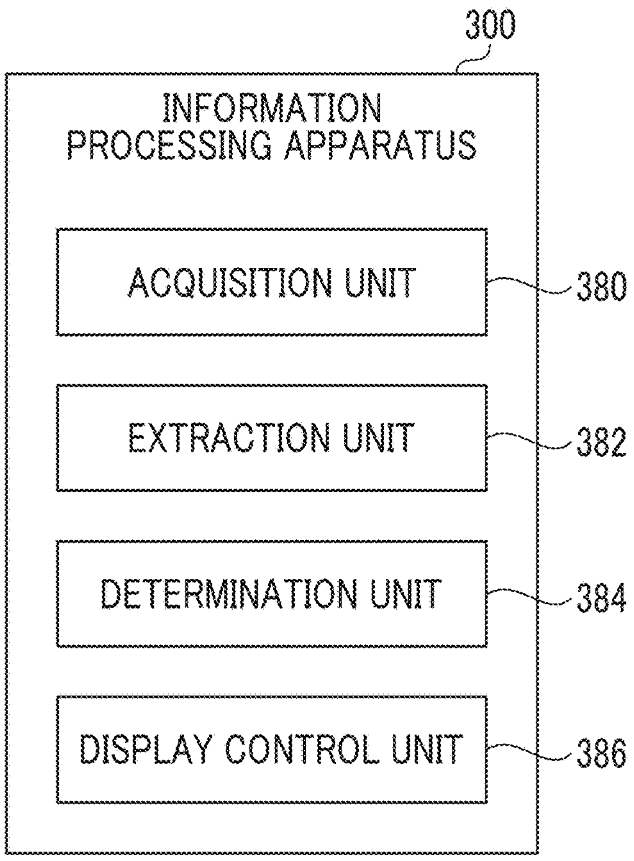
FIG. 6 is a block diagram showing an example of a functional configuration of the information processing apparatus.

An example of a functional configuration of the information processing apparatus 300 will be described with reference to FIG. 6. As shown in FIG. 6, the information processing apparatus 300 includes an acquisition unit 380, an extraction unit 382, a determination unit 384, and a display control unit 386. With the execution of the training program 357 by the CPU 351, the CPU 351 functions as the acquisition unit 380, the extraction unit 382, the determination unit 384, and the display control unit 386.

The acquisition unit 380 acquires a first visual field image 210A showing a visual field of the teacher 12A from the HMD 200A worn by the teacher 12A. Further, the acquisition unit 380 acquires a second visual field image 210B showing the visual field of the student 12B from the HMD 200B worn by the student 12B. Here, the first visual field image 210A and the second visual field image 210B indicate the visual fields of each of the teacher 12A and the student 12B in a case where each of the teacher 12A and the student 12B operates the same type of instrument (for example, the endoscope 16).

Figure 7:
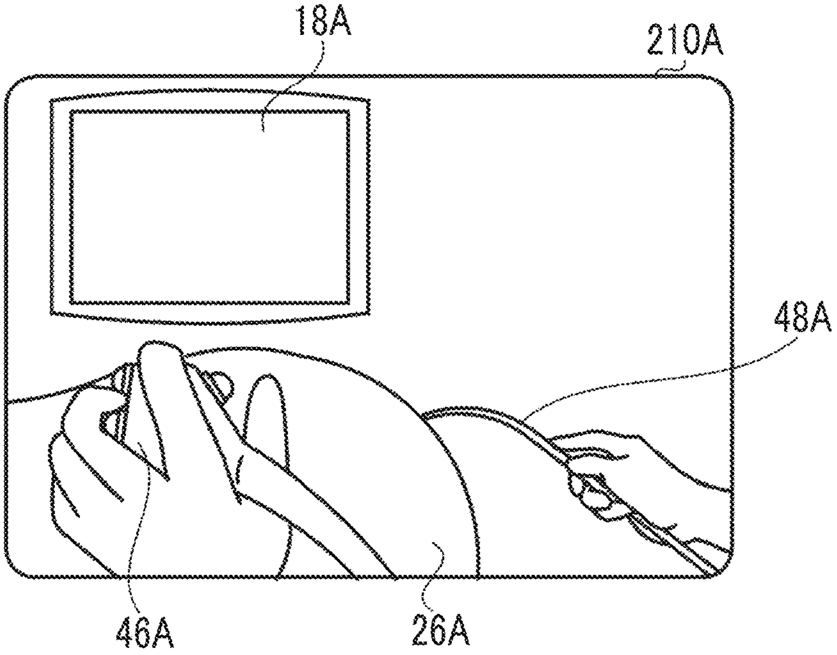
FIG. 7 is a diagram showing an example of a first visual field image of a teacher.
Figure 8:
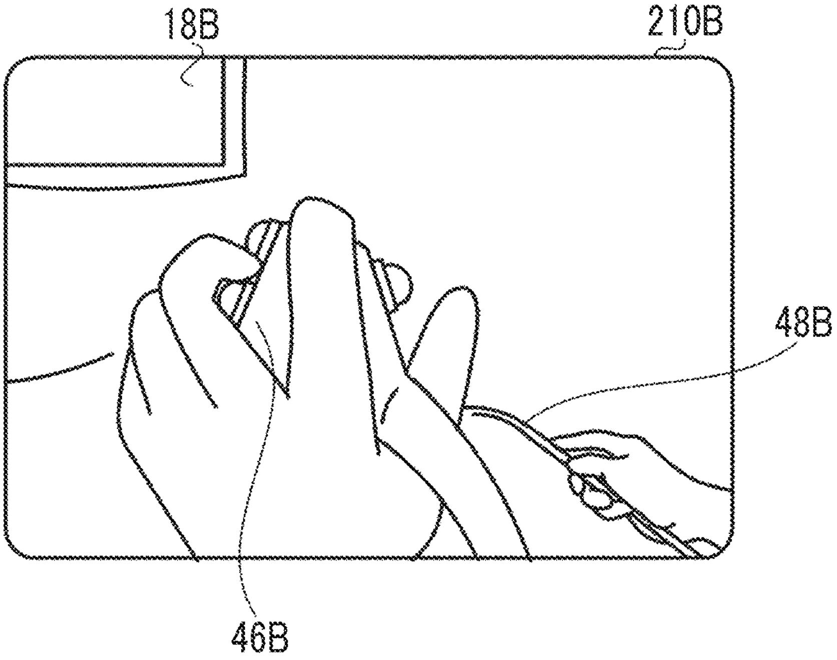
FIG. 8 is a diagram showing an example of a second visual field image of a student.

As an example, FIG. 7 shows the first visual field image 210A showing the visual field of the teacher 12A who is operating the teacher-side endoscope system 10A. FIG. 8 shows the second visual field image 210B showing the visual field of the student 12B who is operating the student-side endoscope system 10B. In general, in the endoscopy, model states such as the holding method of the endoscope 16, a standing position with respect to the subject 26 and the display device 18, and the visual field (an object within field of view and a position thereof) are predetermined. The first visual field image 210A is an appropriate state in which all of the display device 18A, an operation part 46A held in the left hand, an insertion part 48A held in the right hand, and a state of the subject 26A (insertion port) can be visually recognized at the same time. On the other hand, the second visual field image 210B is in an inappropriate state in which the operation part 46B (left hand) is too close to a face and a display device 18B and the subject 26B cannot be visually recognized.

The display control unit 386 performs control of causing the HMD 200B worn by the student 12B to display first interest information indicating a position of the at least one first region of interest included in the first visual field image 210A of the teacher 12A, which is acquired by the acquisition unit 380. That is, the display control unit 386 displays, on the HMD 200B worn by the student 12B, a disposition in which the teacher 12A views the region of interest. Accordingly, the student 12B can view the visual field of the teacher 12A as a reference in a case where the teacher 12A operates the teacher-side endoscope system 10A, and can learn an appropriate operation method of the student-side endoscope system 10B from a difference from the visual field of the student 12B.

Similarly, the display control unit 386 performs control of causing the HMD 200A worn by the teacher 12A to display second interest information indicating a position of at least one second region of interest included in the second visual field image 210B of the student 12B, which is acquired by the acquisition unit 380. That is, the display control unit 386 displays, on the HMD 200A worn by the teacher 12A, a disposition in which the student 12B views the region of interest. Accordingly, the teacher 12A can view the visual field of the student 12B in a case where the student 12B operates the student-side endoscope system 10B, and can point out an inappropriate point or guide the student 12B to a more preferable operation method.

Specifically, the extraction unit 382 may extract at least one first region of interest from the first visual field image 210A. Similarly, the extraction unit 382 may extract at least one second region of interest from the second visual field image 210B. The display control unit 386 may perform control of causing the HMD 200B of the student 12B to display, as the first interest information, information indicating a contour of the at least one first region of interest extracted by the extraction unit 382. Similarly, the display control unit 386 may perform control of causing the HMD 200A of the teacher 12A to display, as the second interest information, information indicating a contour of the at least one extracted second region of interest, which is extracted by the extraction unit 382.

Figure 9:
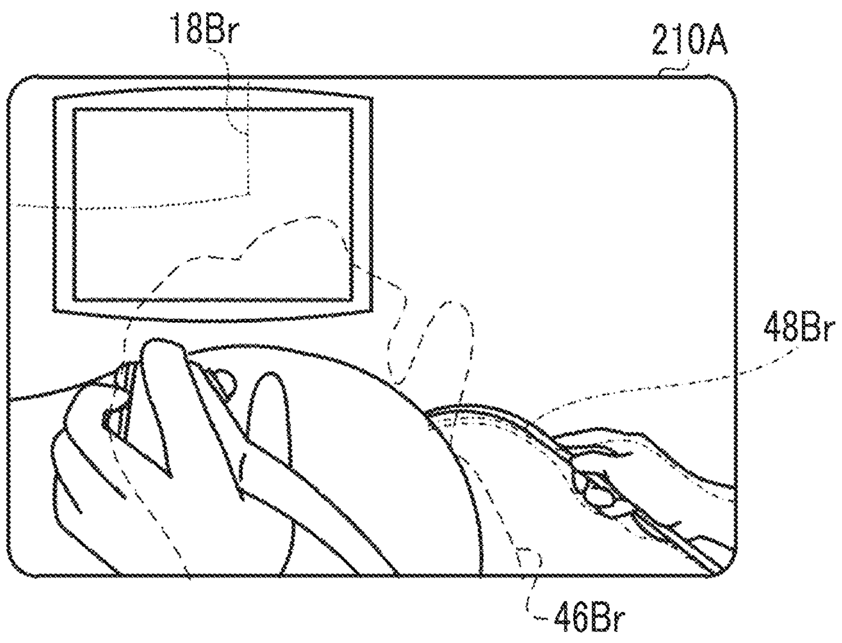
FIG. 9 is a diagram showing an example of an image displayed on the HMD of the teacher.
Figure 10:
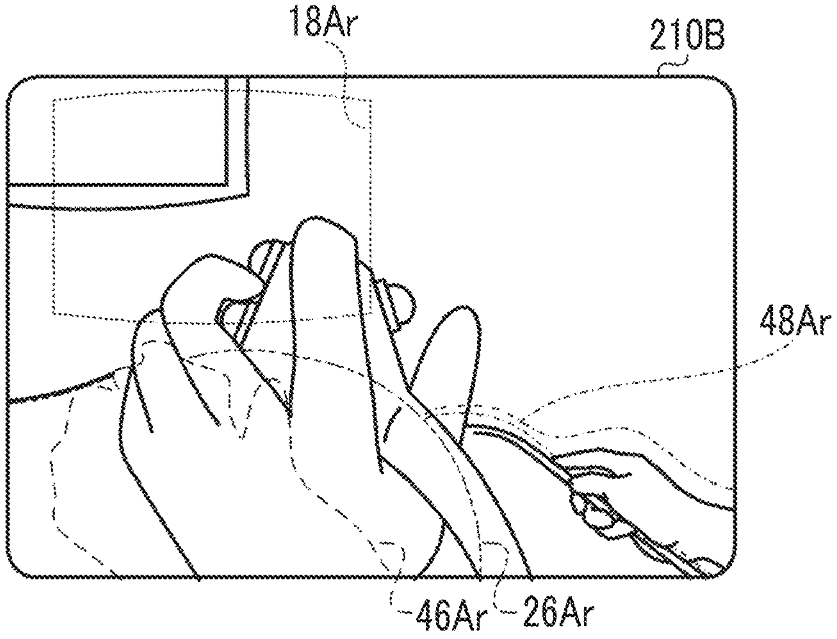
FIG. 10 is a diagram showing an example of an image displayed on the HMD of the student.

As an example, FIG. 9 shows the first visual field image 210A in which the information indicating the contour of the second region of interest, which is displayed on the HMD 200A worn by the teacher 12A, is superimposed. In FIG. 9, the display device 18B (contour 18Br), the operation part 46B (contour 46Br), and an insertion part 48B (contour 48Br) are illustrated as the second region of interest. Further, FIG. 10 shows the second visual field image 210B in which the information indicating the contour of the first region of interest, which is displayed on the HMD 200B worn by the student 12B, is superimposed. In FIG. 10, the display device 18A (contour 18Ar), the operation part 46A (contour 46Ar), the insertion part 48A (contour 48Ar), and the subject 26A (contour 26Ar) are illustrated as the first region of interest.

As shown in FIGS. 9 and 10, each of the first region of interest and the second region of interest may be at least one of a portion of a body (for example, the hand and the foot) of the teacher 12A or the student 12B who operates the instrument, at least a part of the instrument, or a use target (for example, the subject 26) of the instrument. The at least a part of the instrument is, for example, the operation part 46 and the insertion part 48 of the endoscope 16. Further, as shown in FIGS. 9 and 10, a display form for each region of interest may be changed by changing a line type indicating the contour or the like.

Further, in the endoscopy, it is known that a skilled person often first fixes the visual field and then proceeds with the operation by moving only a line of sight without changing an orientation of the face (that is, the visual field is fixed). On the other hand, a beginner tends to proceed with the operation with the face facing the thing (the operation part 46, the insertion part 48, the display device 18, and the like) that is concerned at that time (that is, the visual field fluctuates).

Figure 11:
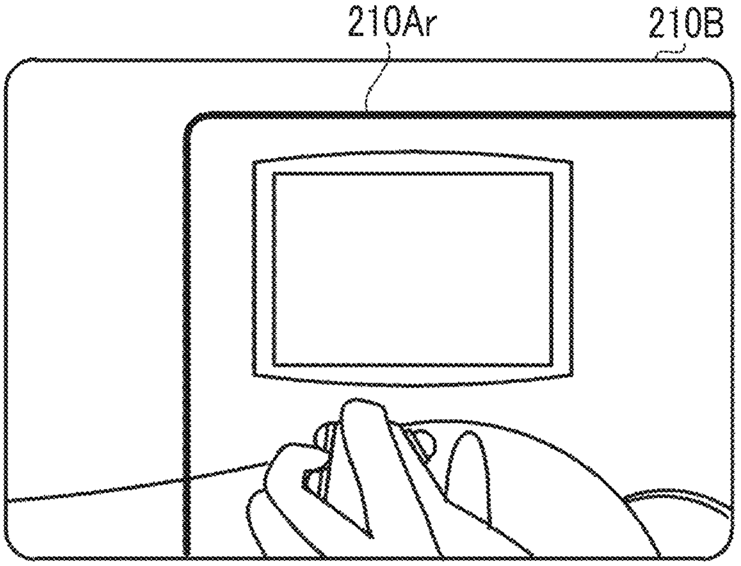
FIG. 11 is a diagram showing an example of an image displayed on the HMD of the student.

As shown in FIG. 11, the first region of interest may be an edge of the first visual field image 210A. In this case, the display control unit 386 may perform control of causing the HMD 200B of the student 12B to display, as the first interest information, information (contour 210Ar) indicating the edge of the first visual field image 210A. According to such a form, the student 12B can notice that the visual field of the student 12B is in a range different from the visual field of the teacher 12A, and thus can return the visual field to an appropriate visual field. Similarly, the second region of interest may be an edge of the second visual field image 210B. In this case, the display control unit 386 may perform control of causing the HMD 200A of the teacher 12A to display, as the second interest information, information indicating the edge of the second visual field image 210B.

In a case where the display unit 254B of the HMD 200B of the student 12B is the non-transmissive type, the display control unit 386 generates a second composite image obtained by combining information indicating the position of the first region of interest of the teacher 12A with the second visual field image 210B of the student 12B captured by a camera 262B of the HMD 200B. The display control unit 386 performs control of causing the display unit 254B to display the generated second composite image. Similarly, in a case where the display unit 254A of the HMD 200A of the teacher 12A is the non-transmissive type, the display control unit 386 generates a first composite image obtained by combining information indicating the position of the second region of interest of the student 12B with the first visual field image 210A of the teacher 12A captured by a camera 262A of the HMD 200A. The display control unit 386 performs control of causing the display unit 254A to display the generated first composite image.

On the other hand, in a case where the display unit 254B of the HMD 200B of the student 12B is the transmissive type, the display control unit 386 controls the display unit 254B to project the information indicating the position of the first region of interest of the teacher 12A. Similarly, in a case where the display unit 254A of the HMD 200A of the teacher 12A is the transmissive type, the display control unit 386 controls the display unit 254A to project the information indicating the position of the second region of interest of the student 12B. That is, in a case where the display unit 254 is the transmissive type, the real space is visually recognized as a real image.

Further, the display control unit 386 may perform control of causing the HMD 200 to display additional information other than the first interest information and the second interest information. Hereinafter, a case where the additional information is displayed on the HMD 200B worn by the student 12B will be described, but the same additional information can also be displayed on the HMD 200A worn by the teacher 12A.

Figure 12:
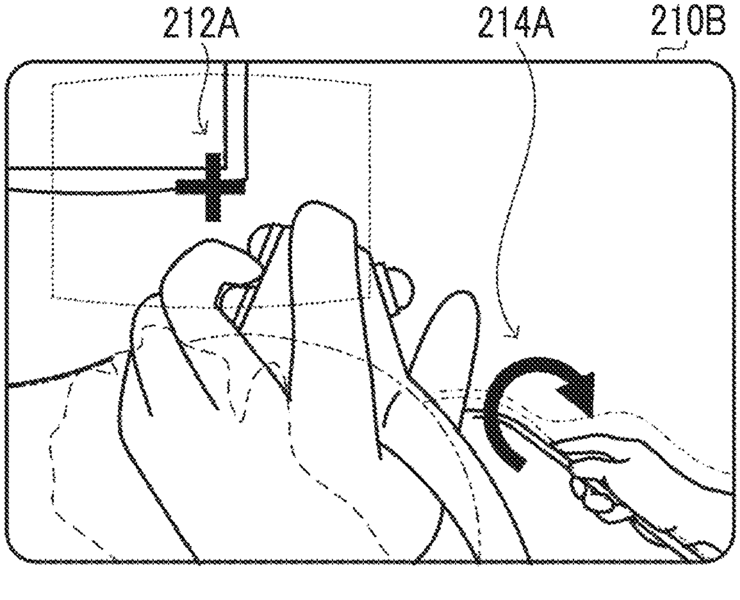
FIG. 12 is a diagram showing an example of a state in which additional information is displayed on the HMD of the student.

For example, as shown in FIG. 12, first visual line information 212A (illustrated by a cross) of the teacher 12A may be displayed in a superimposed manner on the second visual field image 210B of the student 12B. Specifically, the acquisition unit 380 may acquire the first visual line information 212A of the teacher 12A detected by a visual line sensor 261A provided in the HMD 200A of the teacher 12A. The display control unit 386 may perform control of causing the HMD 200B of the student 12B to display the first visual line information 212A of the teacher 12A. According to such a form, the student 12B can ascertain where the teacher 12A gazes at the present time, and thus can deepen the understanding of what kind of operation is required to be performed.

Further, for example, as shown in FIG. 12, rotation information 214A (illustrated by an arrow) indicating a direction in a case where the teacher 12A rotates the insertion part 48A may be displayed in a superimposed manner on the second visual field image 210B of the student 12B. Specifically, the acquisition unit 380 may acquire the first visual field image 210A of the teacher 12A over time. The determination unit 384 may determine whether or not there is a change in the position or the orientation of the first region of interest from the first visual field image 210A acquired by the acquisition unit 380 over time. In a case where the determination by the determination unit 384 is affirmative, the display control unit 386 may perform control of causing the HMD 200B of the student 12B to display information indicating that there is the change in the position or the orientation of the first region of interest. According to such a form, the student 12B can easily determine what kind of operation the teacher 12A has performed, and thus can deepen the understanding of what kind of operation is required to be performed.

Figure 13:
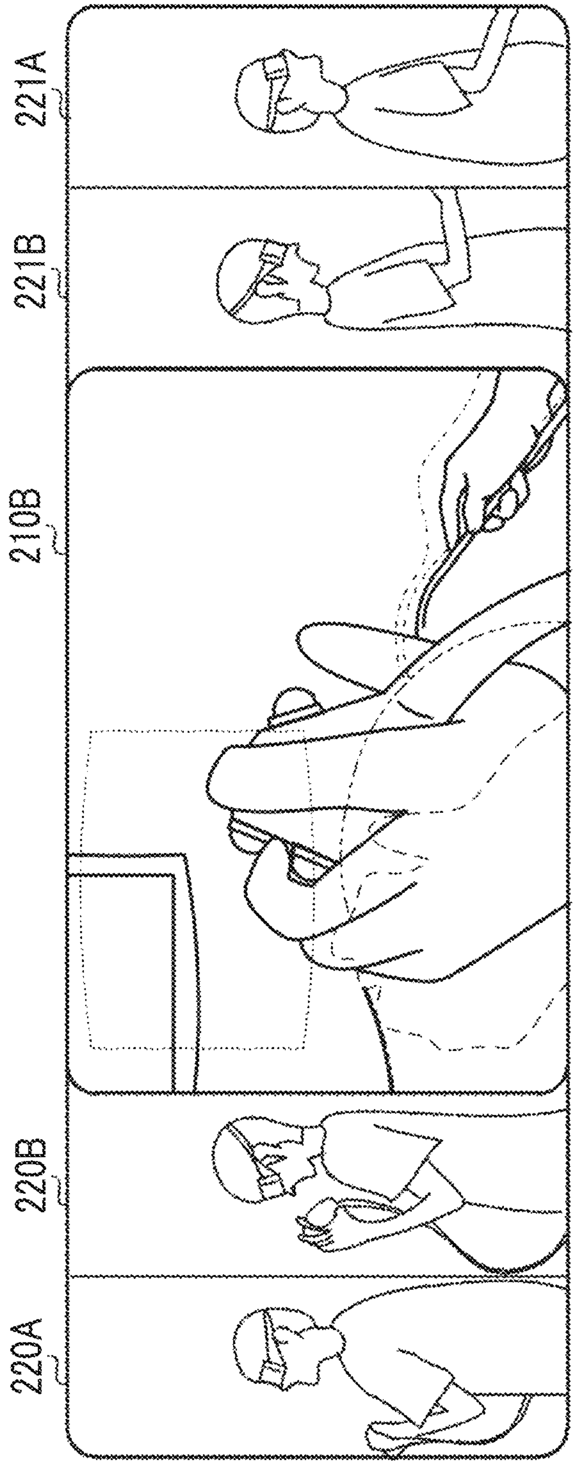
FIG. 13 is a diagram showing an example of a state in which additional information is displayed on the HMD of the student.

Further, for example, as shown in FIG. 13, an image in which postures of the teacher 12A and the student 12B can be recognized may be displayed outside the region in which the visual field of the student 12B is displayed. In the example in FIG. 13, a first posture image 220A and a second posture image 220B, which are obtained by respectively imaging the teacher 12A and the student 12B from a left side, are displayed side by side on a left side. A first posture image 221A and a second posture image 221B, which are obtained by respectively imaging the teacher 12A and the student 12B from a right side, are displayed side by side on a right side. According to such a form, the student 12B can compare the posture of the teacher 12A with the posture of the student 12B, and thus can deepen the understanding of what kind of operation is required to be performed.

Specifically, the acquisition unit 380 may acquire the first posture image of the teacher 12A and the second posture image of the student 12B, which are obtained by respectively imaging the teacher 12A and the student 12B from at least one same direction. The first posture image and the second posture image are captured by, for example, a camera installed on a ceiling, a wall, or the like of a room in which the endoscopy is performed. The display control unit 386 may perform control of causing the first posture image and the second posture image acquired by the acquisition unit 380 to be displayed outside the region in which the visual field of the student 12B is displayed on the HMD 200B of the student 12B.

Figure 14:
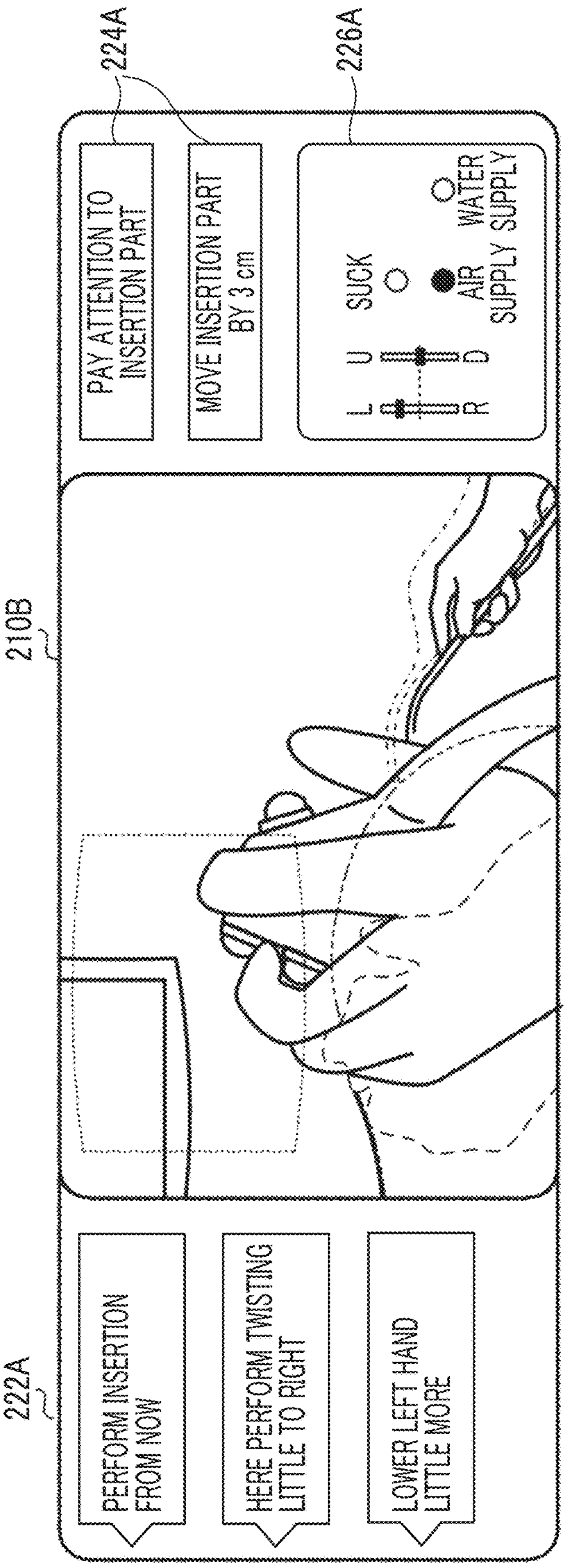
FIG. 14 is a diagram showing an example of a state in which additional information is displayed on the HMD of the student.

Further, for example, as shown on a left side of FIG. 14, an utterance content of the teacher 12A may be displayed, as text information 222A, outside the region in which the visual field of the student 12B is displayed. Specifically, the acquisition unit 380 may acquire a voice of the teacher 12A detected by a microphone 263A of the HMD 200A of the teacher 12A. The display control unit 386 may perform control of converting the voice of the teacher 12A acquired by the acquisition unit 380 into the text information 222A and causing the HMD 200B of the student 12B to display the text information 222A. As a method of converting the voice into the text information, a known method can be appropriately applied. Further, the display control unit 386 may display the utterances of the teacher 12A to flow sequentially from the bottom to the top to make a latest utterance content known. According to such a form, it is possible to suppress the student 12B from failing to hear the utterance content of the teacher 12A, and thus deepen the understanding of what kind of operation is required to be performed.

Further, for example, as shown in an upper right part of FIG. 14, the first visual line information 212A and a history of the operation of the teacher 12A may be displayed, as text information 224A, outside the region in which the visual field of the student 12B is displayed. For example, the display control unit 386 may perform control of performing the image analysis on the first visual field image 210A of the teacher 12A to specify a name (for example, "insertion part") of the thing in front of the visual line indicated by the first visual line information 212A of the teacher 12A, and causing the HMD 200B of the student 12B to display the name as the text information 224A. According to such a form, it is possible to suppress the student 12B from missing the history of the visual line and the operation of the teacher 12A, and thus can deepen the understanding of what kind of operation is required to be performed.

Further, for example, as shown in a lower right part of FIG. 14, parameter information 226A of the endoscope 16A of the teacher 12A may be displayed outside the region in which the visual field of the student 12B is displayed. Specifically, the acquisition unit 380 may acquire the parameter information 226A of the endoscope 16A from the control device 22A of the teacher-side endoscope system 10A. The display control unit 386 may control the HMD 200B of the student 12B to display the parameter information 226A acquired by the acquisition unit 380. According to such a form, the student 12B can easily ascertain what kind of setting and operation the teacher 12A performs at the present time, and thus can deepen the understanding of what kind of operation is required to be performed.

Further, parameter information 226B of the endoscope 16B of the student 12B may be displayed instead of or in addition to the parameter information 226A of the endoscope 16A of the teacher 12A. Specifically, the acquisition unit 380 may acquire the parameter information of the endoscope 16B from the control device 22B of the student-side endoscope system 10B. The display control unit 386 may perform control of causing the HMD 200B of the student 12B to display the parameter information acquired by the acquisition unit 380.

Figure 15:
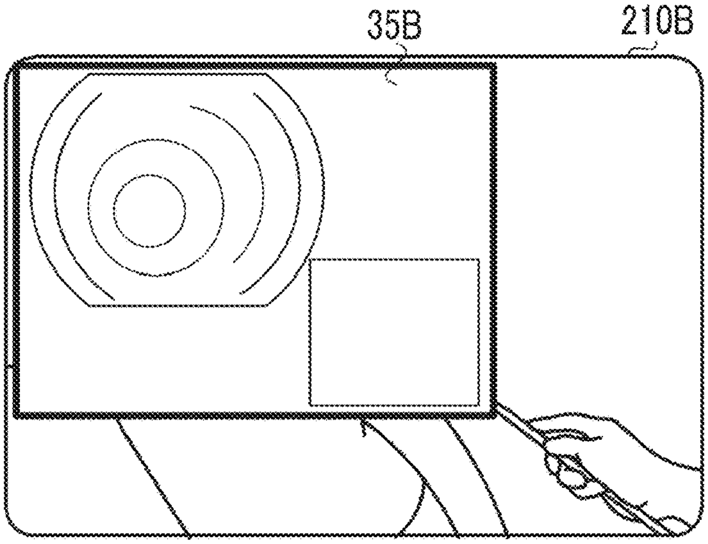
FIG. 15 is a diagram showing an example of a state in which additional information is displayed on the HMD of the student.

Further, for example, as shown in FIG. 15, in a case where the user pays attention to a certain region in the visual field image, control of causing the HMD 200 to display information related to the region may be performed. FIG. 15 shows an example in which, in a case where the student 12B pays attention to the display device 18B in the second visual field image 210B, the screen 35 itself displayed on the display device 18 by the endoscope system 10 is displayed in an enlarged manner on the HMD 200B.

Specifically, the acquisition unit 380 may acquire second visual line information of the student 12B detected by a visual line sensor 261B provided in the HMD 200B of the student 12B. The display control unit 386 may specify a region of interest to be paid attention, which is the second region of interest to which the student 12B pays attention, in the second visual field image 210B, based on the second visual line information of the student 12B acquired by the acquisition unit 380. Further, in a case where the specified region of interest to be paid attention is a predetermined type of region of interest, the display control unit 386 may acquire relevant information related to the region of interest to be paid attention. The display control unit 386 may perform control of superimposing the acquired relevant information on the region of interest to be paid attention and causing the HMD 200B of the student 12B to display the superimposed relevant information.

For example, the second visual line information is assumed to indicate that the student 12B pays attention to the display device 18B. In this case, the display control unit 386 specifies that the display device 18B is the region of interest to be paid attention among the display device 18B, the operation part 46B, and the insertion part 48B, which are the second region of interest included in the second visual field image 210B. In a case where the region of interest to be paid attention is the display device 18B, the display control unit 386 acquires, as the relevant information, information (including the endoscopic video image 39B and the medical information 44B) of the screen 35B displayed on the display device 18B, from the control device 22B of the student-side endoscope system 10B. The display control unit 386 performs control of superimposing the acquired information of the screen 35B on the region (region of interest to be paid attention) of the display device 18B of the second visual field image 210B and causing the HMD 200B of the student 12B to display the superimposed information of the screen 35B. According to such a form, the student 12B can check the information of the screen 35B more clearly than by viewing the screen 35B displayed on the display device 18B.

Further, for example, the second visual line information is assumed to indicate that the student 12B pays attention to the operation part 46B. In this case, the display control unit 386 specifies that the operation part 46B is the region of interest to be paid attention. In a case where the region of interest to be paid attention is the operation part 46B, the display control unit 386 acquires, as the relevant information, the parameter information of the endoscope 16B from the control device 22B of the student-side endoscope system 10B. The display control unit 386 performs control of superimposing the acquired parameter information on the region (region of interest to be paid attention) of the operation part 46B in the second visual field image 210B and causing the HMD 200B of the student 12B to display the superimposed parameter information.

Further, for example, in a case where the region of interest to be paid attention is the operation part 46B, the display control unit 386 may acquire, as the relevant information, an image obtained by capturing the operation part 46B using a camera other than the camera (the camera 262B of the HMD 200B) of the second visual field image 210B. For example, an image captured by a camera that images the operation part 46B from a side surface may be acquired. The display control unit 386 may perform control of superimposing the acquired image on the region (region of interest to be paid attention) of the operation part 46B in the second visual field image 210B and causing the HMD 200B of the student 12B to display the superimposed image.

Further, as shown in FIG. 15, the display control unit 386 may display the relevant information in an enlarged manner. Further, for example, the display control unit 386 may perform enlargement or reduction of the relevant information to be displayed on the HMD 200B, display stop, or the like in response to an instruction from the student 12B. The instruction from the student 12B may be received, for example, by detecting an operation (for example, nodding twice) predetermined for the student 12B by the operation sensor 260B provided in the HMD 200B. Further, for example, a region for instruction may be provided in an end part or the like of the HMD 200B, and the visual line sensor 261B may detect that the visual line is directed to the region for instruction for a predetermined time or longer to receive the instruction. Further, for example, an input unit that does not affect the operation, such as a foot switch, may be used to receive the instruction.

Further, for example, in a case where a phantom is used as the subject 26B, the display control unit 386 may perform control of replacing the region of the subject 26B in the second visual field image 210B with an image of the human body and causing the HMD 200B to display the replaced image. For example, a person's body, face, eyes, and the like may be displayed in the region of the subject 26B in a superimposed manner, and a painful facial expression or a voice indicating that the person is in pain may be output in response to the operation of the student 12B.

Further, for example, in a case where a phantom is used as the subject 26B, the display control unit 386 may perform control of replacing the region of the endoscopic video image 39B in the second visual field image 210B with a large intestine computed tomography (CT) (colonography) image and causing the HMD 200B to display the replaced image. For example, a phantom structure may be associated with the colonography image in advance, and the colonography image corresponding to a position and an orientation of a tip part 50B of the endoscope 16B at the time of insertion may be sequentially displayed. The position and the orientation of the tip part 50B may be detected by, for example, a magnetic sensor or the like.

Further, for example, in a case where a phantom is used as the subject 26B, the display control unit 386 may perform control of replacing the region of the endoscopic video image 39B in the second visual field image 210B with a simulation image including a treatment object such as a polyp and causing the HMD 200B to display the replaced simulation image. Further, in a case where various treatments such as enlargement (air supply) of the inside of the intestine, a residue treatment (water supply and air suction), and polypectomy are performed using a treatment tool 58B in a state in which the simulation image is displayed, the simulation images showing a change in the body may be sequentially displayed.

A plurality of pieces of the above-described additional information may be displayed on the HMD 200B at the same time, or some of the additional information selected by the user may be displayed on the HMD 200B. Further, for example, the additional information displayed on the HMD 200B may be switched by the user at any timing.

Figure 16:
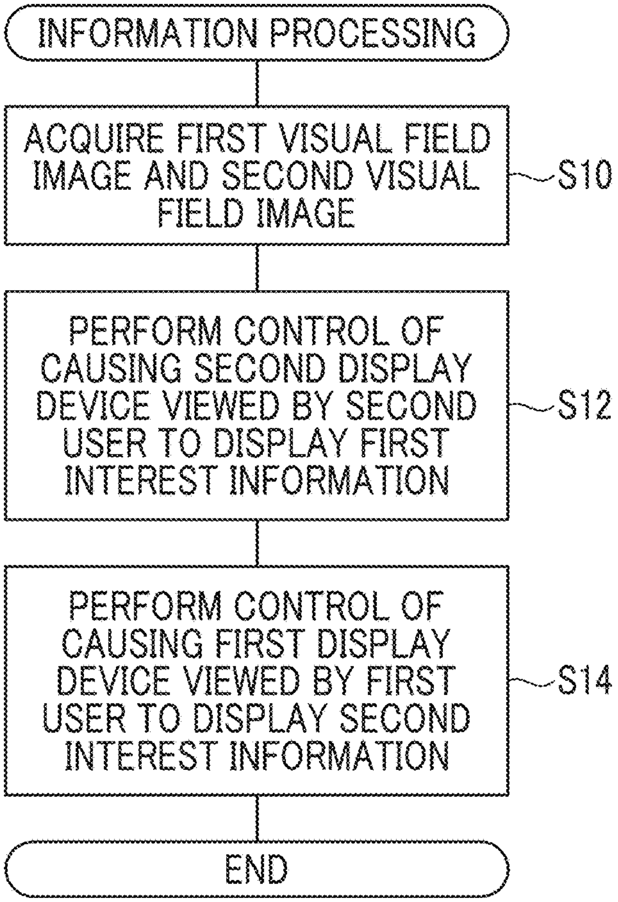
FIG. 16 is a flowchart showing an example of information processing.

Next, an action of the information processing apparatus 300 according to the present embodiment will be described with reference to FIG. 16. In the information processing apparatus 300, the CPU 351 executes the training program 357 to execute information processing shown in FIG. 16. The information processing is executed, for example, in a case where the user gives an instruction to start execution via the operation unit 355.

In step S10, the acquisition unit 380 acquires the first visual field image 210A indicating the visual field of the first user (teacher 12A) and the second visual field image 210B indicating the visual field of the second user (student 12B). In step S12, the display control unit 386 performs control of causing the second display device (HMD 200B), which is viewed by the second user (student 12B), to display the first interest information indicating the position of the at least one first region of interest included in the first visual field image 210A acquired in step S10. In step S14, the display control unit 386 performs control of causing the first display device (HMD 200A), which is viewed by the first user (teacher 12A), to display the second interest information indicating the position of the at least one second region of interest included in the second visual field image 210B acquired in step S10 and ends the present information processing.

As described above, the training system 100 according to one aspect of the present disclosure comprises at least one processor, in which the processor acquires the first visual field image 210A indicating the visual field of the first user (teacher 12A) and the second visual field image 210B indicating the visual field of the second user (student 12B). Further, the processor performs control of causing the second display device (HMD 200B), which is viewed by the second user (student 12B), to display the first interest information indicating the position of at least one first region of interest included in the first visual field image 210A. Further, the processor performs control of causing the first display device (HMD 200A), which is viewed by the first user (teacher 12A), to display the second interest information indicating the position of at least one second region of interest included in the second visual field image 210B.

That is, with the training system 100 of the present disclosure, in a case where the teacher and the student each perform the same operation in parallel, the student can imitate the operation of the teacher or the teacher can give advice on the operation of the student. Therefore, it is possible to perform appropriate training.

The first interest information and the second interest information are not limited to the information indicating the contour of the first region of interest and the information indicating the contour of the second region of interest. Hereinafter, modification examples of the first interest information and the second interest information will be described.

Modification Example 1

The display control unit 386 may perform control of causing the HMD 200B worn by the student 12B to display, as the first interest information, an image in which the first visual field image 210A is made to be semi-transparent. With the display of the semi-transparent first visual field image 210A on the HMD 200B, the student 12B can ascertain the position of the first region of interest in the visual field of the teacher 12A. Similarly, the display control unit 386 may perform control of causing the HMD 200A worn by the teacher 12A to display, as the second interest information, an image in which the second visual field image 210B is made to be semi-transparent. The "image made to be semi-transparent" means an image in a state between transparent (that is, transparency of 100%) and opaque (that is, transparency of 0%), and is not limited to an image in which the transparency is 50%.

Modification Example 2-1

The display control unit 386 may perform control of displaying the pieces of the interest information of the teacher 12A and the student 12B only in a case where a deviation between the visual field of the teacher 12A and the visual field of the student 12B is relatively large. Specifically, the determination unit 384 may associate the first and second regions of interest of the same type with each other and determine whether or not the position of the first region of interest and the position of the second region of interest associated with each other are different from each other. Examples of the first and second regions of interest of the same type include the display devices 18A and 18B, the operation parts 46A and 46B, the insertion parts 48A and 48B, and the subjects 26A and 26B.

Figure 17:
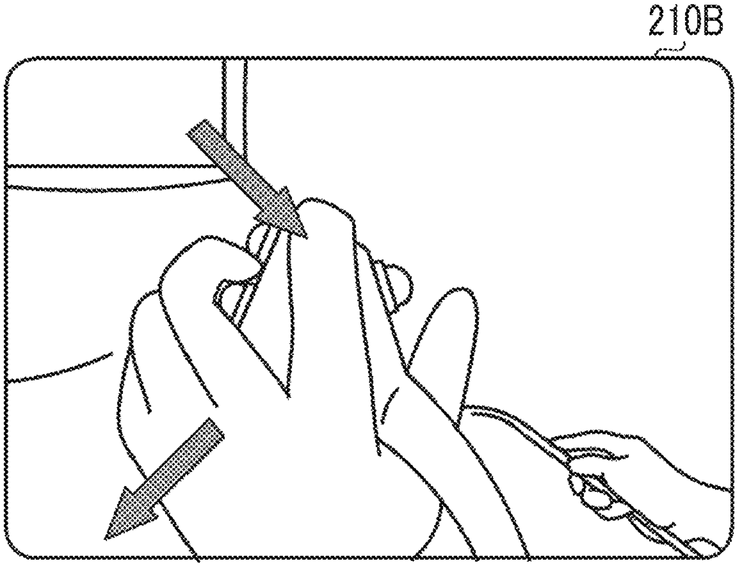
FIG. 17 is a diagram showing an example of an image displayed on the HMD of the student.

In a case where the determination by the determination unit 384 is affirmative (in a case where the deviation is relatively large), the display control unit 386 may perform control of causing the HMD 200B worn by the student 12B to display, as the first interest information, information indicating a difference between the position of the first region of interest and the position of the second region of interest associated with each other. For example, as shown in FIG. 17, the display control unit 386 may represent the difference between the position of the display device 18A (first region of interest) and the position of the display device 18B (second region of interest) by an arrow. Similarly, in a case where the determination by the determination unit 384 is affirmative, the display control unit 386 may perform control of causing the HMD 200A worn by the teacher 12A to display, as the second interest information, information indicating the difference between the position of the first region of interest and the position of the second region of interest associated with each other.

Further, in a case where the determination by the determination unit 384 is negative (in a case where the deviation is relatively small), the display control unit 386 may perform control of causing the HMD 200B worn by the student 12B to display, as the first interest information, the information indicating the difference between the position of the first region of interest and the position of the second region of interest associated with each other in a display form different from the case where the determination by the determination unit 384 is affirmative (in a case where the deviation is relatively large). Specifically, it is preferable that the information indicating the difference is displayed conspicuously as the deviation is larger. For example, in a case where the determination by the determination unit 384 is negative, the arrow as shown in FIG. 17 may not be displayed or a color thereof may be lightened.

Modification Example 2-2

It is assumed that the visual fields are difficult to be aligned even in a case where the visual fields are adjusted according to a difference in physique between the teacher 12A and the student 12B, a difference in environment, and the like. Registration between the visual field of the teacher 12A and the visual field of the student 12B may be performed before the training is started. In a case where the deviation occurs even with the registration, correction may be performed not to be regarded as the deviation in the determination by the determination unit 384.

Specifically, first, the student 12B checks the first interest information of the teacher 12A displayed on the HMD 200B, which is worn by the student 12B, to perform the registration such that the student 12B has the same visual field as the teacher 12A as much as possible. A point in time at which the registration is completed is set as an initial point in time. Whether or not the registration is completed may be determined by the determination unit 384 based on, for example, the deviation between the first visual field image 210A and the second visual field image 210B, or the user may input that the registration is completed.

The acquisition unit 380 acquires the first visual field image 210A and the second visual field image 210B at the initial point in time. The extraction unit 382 extracts the first region of interest from the first visual field image 210A at the initial point in time and extracts the second region of interest from the second visual field image 210B at the initial point in time. The determination unit 384 derives, as a correction value, the difference between the positions of the associated first and second regions of interest, which are extracted respectively from the first visual field image 210A and the second visual field image 210B at the initial point in time. For example, the determination unit 384 derives that, at the initial point in time, the display device 18B deviates from the display device 18A by 5 cm in a left direction and the operation part 46B deviates from the operation part 46A by 5 cm in a right direction.

Thereafter, even while the teacher 12A and the student 12B each progress the operation, the acquisition unit 380 acquires the first visual field image 210A and the second visual field image 210B over time. The extraction unit 382 extracts the first region of interest from each of the first visual field images 210A acquired over time, and extracts the second region of interest from each of the second visual field images 210B acquired over time.

The determination unit 384 derives a difference obtained by correcting, using the correction value, the difference between the positions of the associated first and second regions of interest, which are extracted respectively from the first visual field image 210A and the second visual field image 210B at a point in time later than the initial point in time. For example, at a certain point in time after the start of the training, in a case where the display device 18B deviates from the display device 18A by 5 cm in the left direction, the deviation is the same as the deviation at the initial point in time. Thus, the determination unit 384 derives the difference as 0 cm. On the other hand, in a case where the operation part 46B deviates from the operation part 46A in the right direction by 10 cm, the deviation is larger than the deviation at the initial point in time. Thus, the determination unit 384 derives the difference as 5 cm in the right direction. The determination unit 384 determines whether or not the position of the first region of interest and the position of the second region of interest are different from each other based on the difference corrected by using the correction value derived based on the deviation at the initial point in time.

Modification Example 3

Figure 18:
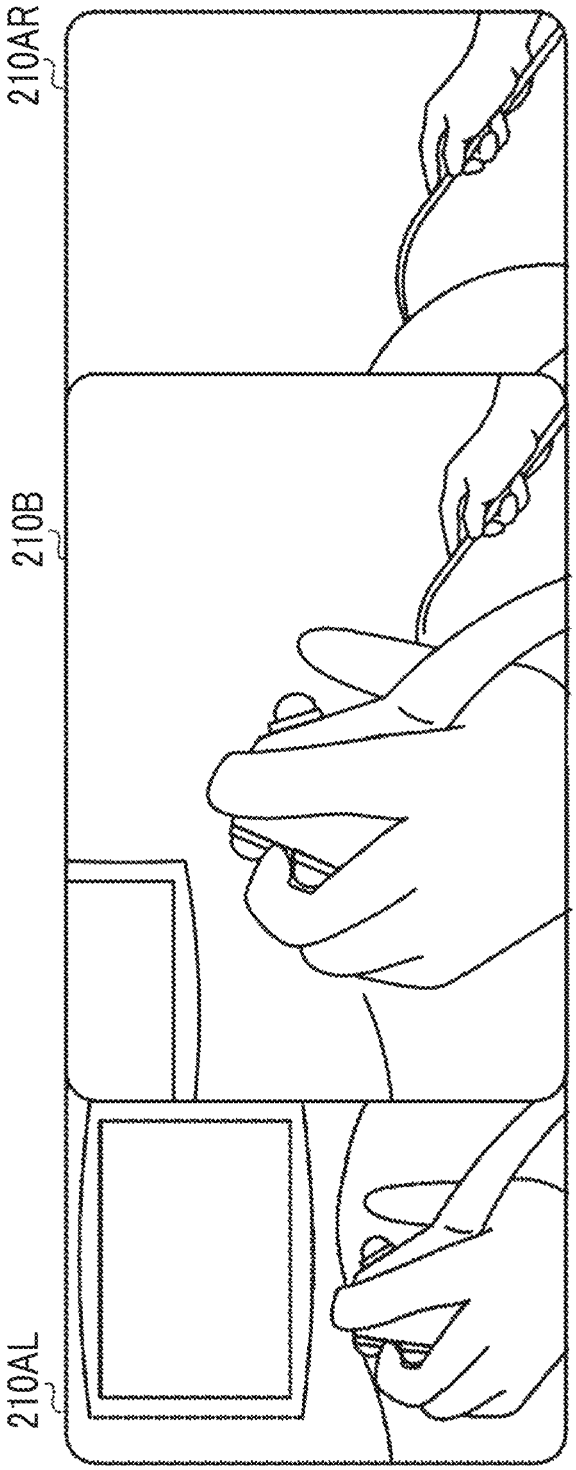
FIG. 18 is a diagram showing an example of an image displayed on the HMD of the student.

In the above description, the form has been described in which the second interest information is displayed to be superimposed on the first visual field image 210A and the first interest information is displayed to be superimposed on the second visual field image 210B, but the present disclosure is not limited thereto. For example, as shown in FIG. 18, the visual field image of the other person may be divided and displayed on left and right sides of the visual field of the user. In FIG. 18, the first visual field image 210A of the teacher 12A is displayed in a divided manner on the left and right sides of the second visual field image 210B of the student 12B.

Specifically, the display control unit 386 may perform control of displaying, as the first interest information, an image 210AL on the left side of the images obtained by dividing the first visual field image 210A into two parts of left and right on a left side of the region in which the visual field of the student 12B is displayed in the HMD 200B. Further, the display control unit 386 may perform control of displaying, as the first interest information, an image 210AR on the right side of the images obtained by dividing the first visual field image 210A into two parts of left and right on a right side of the region in which the visual field of the student 12B is displayed in the HMD 200B.

Similarly, the display control unit 386 may perform control of displaying, as the second interest information, an image on the left side of the images obtained by dividing the second visual field image 210B into two parts of left and right on a left side of the region in which the visual field of the teacher 12A is displayed in the HMD 200A. Further, the display control unit 386 may perform control of displaying, as the second interest information, an image on the right side of the images obtained by dividing the second visual field image 210B into two parts of left and right on a right side of the region in which the visual field of the teacher 12A is displayed in the HMD 200A.

Here, the region in which the visual field of the student 12B (teacher 12A) is displayed in the HMD 200 is, for example, a region in which the user visually recognizes the real space via a lens (display) in a case where the HMD 200 is the transmissive type. Further, for example, in a case where the HMD 200 is the non-transmissive type, the region in which the visual field of the student 12B (teacher 12A) is displayed in the HMD 200 is a region in which an image (visual field image) of the real space captured by the camera 262 is displayed.

Further, in the above embodiment, the form of the second interest information displayed on the HMD 200A of the teacher 12A may not be the same as the form of the first interest information displayed on the HMD 200B of the student 12B. For example, the HMD 200A of the teacher 12A may be displayed in the form as shown in FIG. 9, and the HMD 200B of the student 12B may be displayed in the form as shown in FIG. 18. The display form may be predetermined or may be randomly selected by the user.

Further, in the above embodiment described above, the form has been described in which the first visual field image 210A and the second visual field image 210B are captured by the camera 262 provided in the HMD 200, but the present disclosure is not limited thereto. For example, the first visual field image 210A and/or the second visual field image 210B may be acquired by using a camera provided at any place of a wall, a ceiling, or the like of a room in which the user performs the training, and a camera mounted on any portion of the head, the shoulder, the chest, or the like of the user. Further, for example, these external cameras and the camera 262 provided in the HMD 200 may be combined to generate the visual field image in a wider range. Further, for example, the image displayed on the display unit 254 of the HMD 200 may be captured by using the camera of the HMD 200, and the image used for the extraction of the first region of interest and the second region of interest may be captured by using the external camera.

Figure 19:
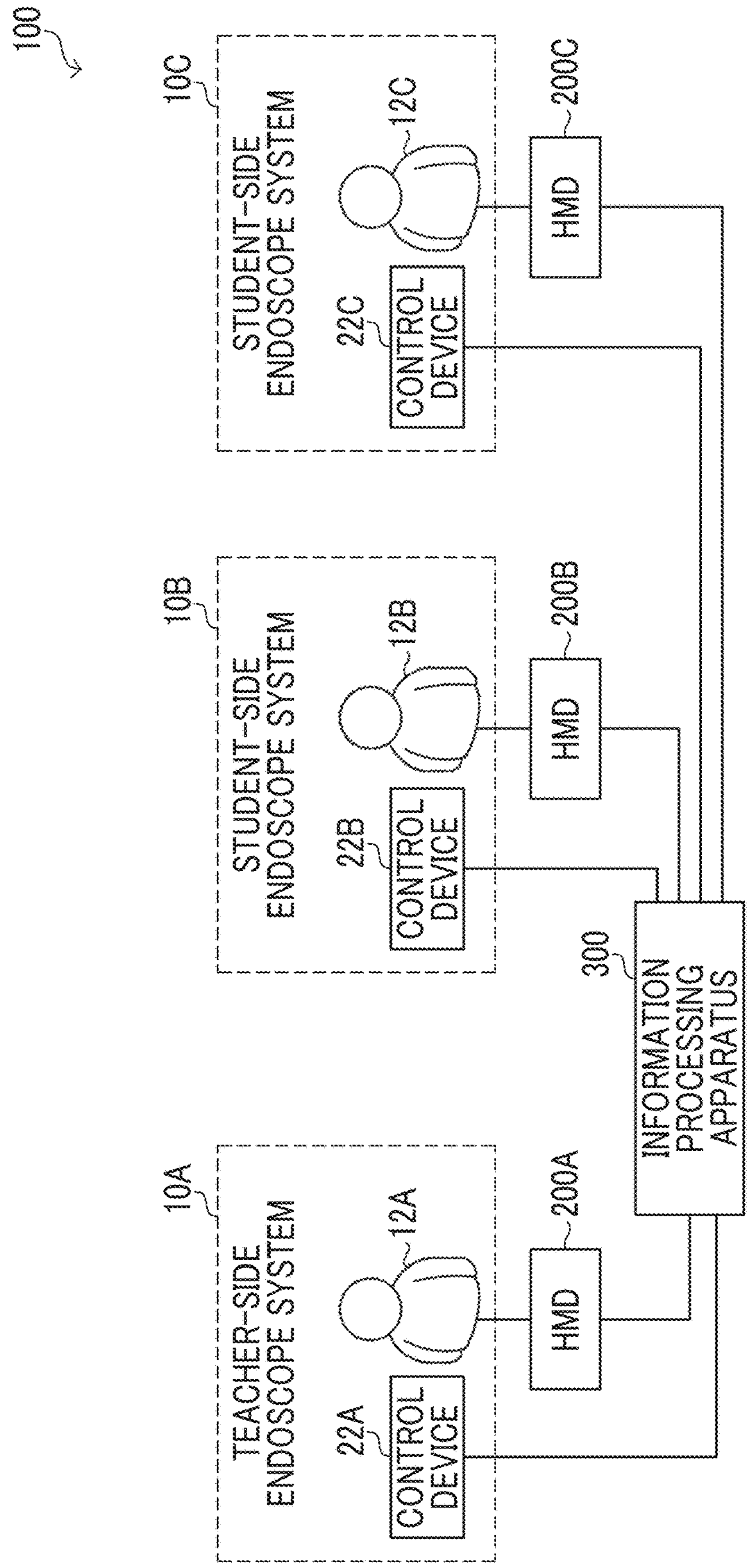
FIG. 19 is a schematic diagram showing an example of an overall configuration of the training system in a case where there are a plurality of students.

Further, in the above embodiment described above, the form has been described in which one teacher 12A and one student 12B perform the training, but the present disclosure is not limited thereto. For example, as shown in FIG. 19, the training system 100 of the present disclosure can be applied even in a case where a plurality of students 12B and 12C are trained by one teacher 12A.

That is, the display control unit 386 may perform control of causing an HMD 200C worn by the student 12C, which is different from the student 12B, to display the first interest information included in the first visual field image 210A of the teacher 12A. In this case, the HMD 200A of the teacher 12A may display the second interest information indicating the position of the second region of interest included in the second visual field image 210B of the student 12B, or may display third interest information indicating a position of a third region of interest included in a third visual field image of the student 12C. Further, the second interest information and the third interest information may be displayed at the same time, or may be displayed in a switchable manner in response to an instruction from the teacher 12A. The student 12C is an example of a third user according to the present disclosure, and the HMD 200C is an example of a third display device viewed by the third user according to the present disclosure.

Further, as shown in FIG. 1, in the endoscope system 10, there may be a case where the operation is performed with assistance from the nurse 14 or the like. For example, in a case where the polypectomy is performed, the doctor 12 operates the operation part 46 and the insertion part 48 to guide the tip part 50 of the endoscope 16 to the polyp, and the nurse pushes the treatment tool 58 in response to a doctor's call.

Figure 20:
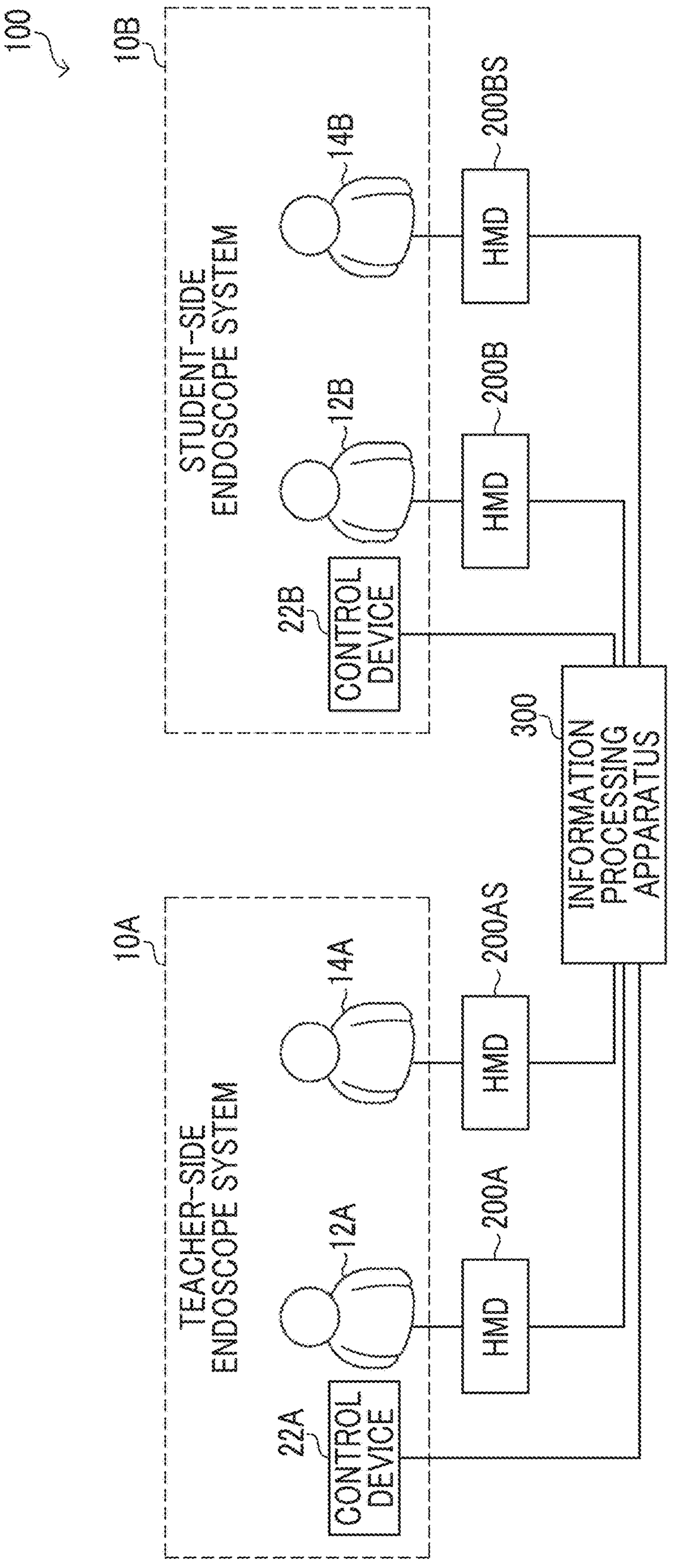
FIG. 20 is a schematic diagram showing an example of an overall configuration of the training system in a case where training is performed in pairs.

As shown in FIG. 20, the training system 100 of the present disclosure enables the training using a teacher pair and a student pair, and is also suitable for the above-described collaboration work. In FIG. 20, a pair of the teacher 12A (doctor) and a sub-teacher 14A (nurse), and a pair of the student 12B (doctor) and a sub-student 14B (nurse) perform the training. That is, in a case where the doctors perform the same operation with each other and the nurses each perform the same operation with each other in parallel, the student can imitate the operation of the teacher or the teacher can give advice on the operation of the student.

In this case, the acquisition unit 380 may acquire a first sub-visual field image showing the visual field of the sub-teacher 14A and a second sub-visual field image showing the visual field of the sub-student 14B. The display control unit 386 may perform control of causing an HMD 200BS, which is worn by the sub-student 14B, to display information indicating a position of a first sub-region of interest included in the first sub-visual field image of the sub-teacher 14A. Further, the display control unit 386 may perform control of causing an HMD 200AS, which is worn by the sub-teacher 14A, to display information indicating a position of a second sub-region of interest included in the second sub-visual field image of the sub-student 14B. The sub-teacher 14A is an example of a first sub-user of the present disclosure, and the sub-student 14B is an example of a second sub-user of the present disclosure. The HMD 200AS is an example of a first sub-display device viewed by the first sub-user of the present disclosure, and the HMD 200BS is an example of a second sub-display device viewed by the second sub-user of the present disclosure.

Further, in this case, visual field sharing between the pairs may be performed in addition to the visual field sharing between the teacher and the student. That is, for example, the HMD 200B of the student 12B (doctor) may be controlled to display information indicating the respective positions of the first region of interest of the teacher 12A (doctor) and the second sub-region of interest of the sub-student 14B (nurse) who is the pair of the student 12B (doctor). Specifically, the acquisition unit 380 may acquire the second sub-visual field image showing the visual field of the sub-student 14B. The display control unit 386 may perform control of causing the HMD 200B of the student 12B (doctor) to display the first interest information of the teacher 12A (doctor) and the information indicating the position of the second sub-region of interest included in the second sub-visual field image of the sub-student 14B (nurse).

Further, in the above embodiment described above, the form example has been described in which the HMD 200 is applied as the first display device viewed by the first user, the second display device viewed by the second user, the third display device viewed by the third user, the first sub-display device viewed by the first sub-user, and the second sub-display device viewed by the second sub-user, but the present disclosure is not limited thereto. As the display device viewed by each user of the present disclosure, for example, various portable displays such as a glasses-type wearable device (so-called smart glasses) and a contact lens-type wearable device (so-called smart contact lens) may be applied. Further, for example, a stationary display disposed near each user may be applied. Further, for example, a screen that is suspended from a ceiling of a room where each user stays or a projector that projects an image to a wall of the room may be applied. Further, for example, AR glasses that are suspended from a ceiling of a room where each user stays may be applied, and each user may look into the AR glasses. Further, for example, an aerial display that forms an image in the air may be applied. Further, the type of the display device viewed by each user may be different. For example, the stationary display may be applied as the first display device viewed by the first user, and the HMD 200 may be applied as the second display device viewed by the second user.

Further, in the above embodiment, the control device 22 or the like of the endoscope system 10 may include a part or all of the functions of the information processing apparatus 300, such as the acquisition unit 380, the extraction unit 382, the determination unit 384, and the display control unit 386.

Further, in the above embodiment, for example, as hardware structures of processing units that execute various types of processing, such as the acquisition unit 380, the extraction unit 382, the determination unit 384, and the display control unit 386, various processors shown below can be used. As described above, in addition to the CPU that is a general-purpose processor that executes software (program) to function as various processing units, the various processors include a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured by using one of the various processors or may be configured by using a combination of two or more processors of the same type or different types (for example, a combination of a plurality of FPGAs or a combination of a CPU and an FPGA). Moreover, a plurality of processing units may be configured of one processor.

As an example of configuring the plurality of processing units with one processor, first, there is a form in which one processor is configured by a combination of one or more CPUs and software and the processor functions as the plurality of processing units, as represented by computers such as a client and a server. Second, as represented by a system-on-chip (SoC) or the like, there is a form in which the processor is used in which the functions of the entire system which includes the plurality of processing units are realized by a single integrated circuit (IC) chip. In this manner, the various processing units are configured using one or more of the various processors as a hardware structure.

Further, more specifically, a circuitry combining circuit elements such as semiconductor elements can be used as the hardware structure of the various processors.

Further, in the above embodiment, the form has been described in which the various programs in the information processing apparatus 300 and the HMD 200 are stored in the storage unit in advance, but the present disclosure is not limited thereto. The various programs may be provided in a form of being recorded on a recording medium such as a compact disc read only memory (CD-ROM), a digital versatile disc read only memory (DVD-ROM), and a Universal Serial Bus (USB) memory. The various programs may be provided in a form of being downloaded from an external device via a network. Furthermore, the technique of the present disclosure extends to a storage medium that stores the program non-transitorily, in addition to the program.

In the technique of the present disclosure, the embodiment and the examples described above can be combined as appropriate. The above-described contents and the above-shown contents are detailed descriptions for parts according to the technique of the present disclosure, and are merely examples of the technique of the present disclosure. For example, the descriptions regarding the configurations, the functions, the actions, and the effects are descriptions regarding an example of the configurations, the functions, the actions, and the effects of the part according to the technique of the present disclosure. Accordingly, in the contents described and the contents shown hereinabove, it is needless to say that removal of an unnecessary part, or addition or replacement of a new element may be employed within a range not departing from the gist of the technique of the present disclosure.

Regarding the above embodiment, the following Supplementary Notes are further disclosed.

Supplementary Note 1

An information processing system comprising:

at least one processor, wherein the processor is configured to:

acquire a first visual field image showing a visual field of a first user and a second visual field image showing a visual field of a second user;

perform control of causing a second display device viewed by the second user to display first interest information indicating a position of at least one first region of interest included in the first visual field image; and perform control of causing a first display device viewed by the first user to display second interest information indicating a position of at least one second region of interest included in the second visual field image.

Supplementary Note 2

The information processing system according to Supplementary Note 1, wherein the processor is configured to:

perform control of causing the second display device to display, as the first interest information, an image in which the first visual field image is made to be semi-transparent.

Supplementary Note 3

The information processing system according to Supplementary Note 1 or 2, wherein the processor is configured to:

extract the at least one first region of interest from the first visual field image; and perform control of causing the second display device to display, as the first interest information, information indicating a contour of the extracted at least one first region of interest.

Supplementary Note 4

The information processing system according to any one of Supplementary Notes 1 to 3, wherein the processor is configured to:

extract the at least one first region of interest from the first visual field image;

extract the at least one second region of interest from the second visual field image;

associate the first region of interest and the second region of interest of the same type with each other;

determine whether or not positions of the associated first and second regions of interest are different from each other; and perform control of causing, in a case where the determination is affirmative, the second display device to display, as the first interest information, information indicating a difference between the positions of the associated first and second regions of interest.

Supplementary Note 5

The information processing system according to Supplementary Note 4, wherein the processor is configured to:

perform control of causing, in a case where the determination is negative, the second display device to display, as the first interest information, the information indicating the difference between the positions of the associated first and second regions of interest in a display form different from the case where the determination is affirmative.

Supplementary Note 6

The information processing system according to Supplementary Note 4 or 5, wherein the processor is configured to:

acquire the first visual field image and the second visual field image over time;

derive, as a correction value, the difference between the positions of the associated first and second regions of interest, which are extracted respectively from the first visual field image and the second visual field image at an initial point in time; and perform the determination based on a difference obtained by correcting, using the correction value, the difference between the positions of the associated first and second regions of interest, which are extracted respectively from the first visual field image and the second visual field image at a point in time later than the initial point in time.

Supplementary Note 7

The information processing system according to any one of Supplementary Notes 1 to 6, wherein the processor is configured to:

perform control of displaying, as the first interest information, an image on a left side among images obtained by dividing the first visual field image into two parts of left and right on a left side of a region in which the visual field of the second user is displayed on the second display device; and perform control of displaying, as the first interest information, an image on a right side among the images obtained by dividing the first visual field image into two parts of left and right on a right side of the region in which the visual field of the second user is displayed on the second display device.

Supplementary Note 8

The information processing system according to any one of Supplementary Notes 1 to 7, wherein the processor is configured to:

acquire the first visual field image over time;

determine whether or not there is a change in a position or an orientation of the first region of interest from the first visual field image acquired over time; and perform control of causing, in a case where the determination is affirmative, the second display device to display information indicating that there is the change in the position or the orientation of the first region of interest.

Supplementary Note 9

The information processing system according to any one of Supplementary Notes 1 to 8, wherein the processor is configured to:

acquire first visual line information of the first user; and perform control of causing the second display device to display the first visual line information of the first user.

Supplementary Note 10

The information processing system according to any one of Supplementary Notes 1 to 9, wherein the processor is configured to:

acquire second visual line information of the second user;

specify, based on the second visual line information, a region of interest to be paid attention that is the second region of interest to which the second user pays attention in the second visual field image;

acquire, in a case where the region of interest to be paid attention is a predetermined type of region of interest, relevant information related to the region of interest to be paid attention; and perform control of causing the second display device to display the relevant information on the region of interest to be paid attention in a superimposed manner.

Supplementary Note 11

The information processing system according to any one of Supplementary Notes 1 to 10, wherein the processor is configured to:

acquire a first posture image and a second posture image obtained by respectively imaging the first user and the second user in at least one same direction; and perform control of displaying the first posture image and the second posture image on an outside of a region in which the visual field of the second user is displayed on the second display device.

Supplementary Note 12

The information processing system according to any one of Supplementary Notes 1 to 11, wherein the processor is configured to:

acquire a voice of the first user;

convert the voice of the first user into text information; and perform control of causing the second display device to display the text information.

Supplementary Note 13

The information processing system according to any one of Supplementary Notes 1 to 12, wherein the processor is configured to:

generate a second composite image obtained by combining the second visual field image with the information indicating the position of the first region of interest;

generate a first composite image obtained by combining the first visual field image with the information indicating the position of the second region of interest;

perform control of causing the second display device to display the second composite image; and perform control of causing the first display device to display the first composite image.

Supplementary Note 14

The information processing system according to any one of Supplementary Notes 1 to 13, wherein the first visual field image and the second visual field image indicate the visual fields of the first user and the second user in a case where the first user and the second user operate the same type of instrument, and each of the first region of interest and the second region of interest is at least one of a portion of a body of the first user or the second user who operates the instrument, at least a part of the instrument, a use target of the instrument, or an edge of the first visual field image or the second visual field image.

Supplementary Note 15

The information processing system according to Supplementary Note 14, wherein the processor is configured to:

acquire parameter information related to the instrument; and perform control of causing the second display device to display the parameter information.

Supplementary Note 16

The information processing system according to any one of Supplementary Notes 1 to 15, wherein the processor is configured to:

perform control of causing a third display device viewed by a third user to display the first interest information.

Supplementary Note 17

The information processing system according to any one of Supplementary Notes 1 to 16, wherein the processor is configured to:

acquire a first sub-visual field image showing a visual field of a first sub-user and a second sub-visual field image showing a visual field of a second sub-user;

perform control of causing a second sub-display device viewed by the second sub-user to display information indicating a position of a first sub-region of interest included in the first sub-visual field image; and perform control of causing a first sub-display device viewed by the first sub-user to display information indicating a position of a second sub-region of interest included in the second sub-visual field image.

Supplementary Note 18

The information processing system according to any one of Supplementary Notes 1 to 17, wherein the processor is configured to:

acquire a second sub-visual field image showing a visual field of a second sub-user; and perform control of causing the second display device to display the first interest information and information indicating a position of a second sub-region of interest included in the second sub-visual field image.

Supplementary Note 19

An information processing method executed by a computer, the information processing method comprising:

acquiring a first visual field image showing a visual field of a first user and a second visual field image showing a visual field of a second user;

performing control of causing a second display device viewed by the second user to display first interest information indicating a position of at least one first region of interest included in the first visual field image; and performing control of causing a first display device viewed by the first user to display second interest information indicating a position of at least one second region of interest included in the second visual field image.

Supplementary Note 20

An information processing program causing a computer to execute a process comprising:

acquiring a first visual field image showing a visual field of a first user and a second visual field image showing a visual field of a second user;

performing control of causing a second display device viewed by the second user to display first interest information indicating a position of at least one first region of interest included in the first visual field image; and performing control of causing a first display device viewed by the first user to display second interest information indicating a position of at least one second region of interest included in the second visual field image.

What is claimed is:

1. An information processing system comprising at least one processor, wherein the at least one processor is configured to:

acquire a first visual field image showing a visual field of a first user and a second visual field image showing a visual field of a second user;

perform control of causing a second display device viewed by the second user to display first interest information indicating a position of at least one first region of interest included in the first visual field image; and perform control of causing a first display device viewed by the first user to display second interest information indicating a position of at least one second region of interest included in the second visual field image, wherein the first visual field image and the second visual field image indicate the visual fields of the first user and the second user in a case where the first user and the second user operate the same type of instrument, and wherein each of the at least one first region of interest and the at least one second region of interest at least one of a portion of a body of the first user or the second user who operates the instrument, at least a part of the instrument, a use target of the instrument, or an edge of the first visual field image or the second visual field image.

2. The information processing system according to claim 1, wherein the at least one processor is configured to perform control of causing the second display device to display, as the first interest information, an image in which the first visual field image is made to be semi-transparent.

3. The information processing system according to claim 1, wherein the at least one processor is configured to:

extract the at least one first region of interest from the first visual field image; and perform control of causing the second display device to display, as the first interest information, information indicating a contour of the extracted at least one first region of interest.

4. An information processing system comprising at least one processor, wherein the at least one processor is configured to:

acquire a first visual field image showing a visual field of a first user and a second visual field image showing a visual field of a second user;

perform control of causing a second display device viewed by the second user to display first interest information indicating a position of at least one first region of interest included in the first visual field image;

perform control of causing a first display device viewed by the first user to display second interest information indicating a position of at least one second region of interest included in the second visual field image;

extract the at least one first region of interest from the first visual field image;

extract the at least one second region of interest from the second visual field image;

associate a first region of interest and a second region of interest of a same type with each other;

make a determination as to whether or not positions of the associated first region of interest and second region of interest are different from each other; and perform control of causing, in a case where the determination is affirmative, the second display device to display, as the first interest information, information indicating a difference between the positions of the associated first region of interest and second region of interest.

5. The information processing system according to claim 4, wherein the at least one processor is configured to perform control of causing, in a case where the determination is negative, the second display device to display, as the first interest information, the information indicating the difference between the positions of the associated first region of interest and second region of interest, in a display form different from the case where the determination is affirmative.

6. The information processing system according to claim 4, wherein the at least one processor is configured to:

acquire the first visual field image and the second visual field image over time;

derive, as a correction value, the difference between the positions of the associated first region of interest and second region of interest, which are extracted respectively from the first visual field image and the second visual field image at an initial point in time; and perform the determination based on a difference obtained by correcting, using the correction value, the difference between the positions of the associated first region of interest and second region of interest, which are extracted respectively from the first visual field image and the second visual field image at a point in time later than the initial point in time.

7. The information processing system according to claim 1, wherein the at least one processor is configured to:

perform control of displaying, as the first interest information, an image on a left side among images obtained by dividing the first visual field image into two parts of left and right on a left side of a region in which the visual field of the second user is displayed on the second display device; and perform control of displaying, as the first interest information, an image on a right side among the images obtained by dividing the first visual field image into two parts of left and right on a right side of the region in which the visual field of the second user is displayed on the second display device.

8. The information processing system according to claim 1, wherein the at least one processor is configured to:

acquire the first visual field image over time;

make a determination as to whether or not there is a change in a position or an orientation of the at least one first region of interest from the first visual field image acquired over time; and perform control of causing, in a case where the determination is affirmative, the second display device to display information indicating that there is the change in the position or the orientation of the at least one first region of interest.

9. The information processing system according to claim 1, wherein the at least one processor is configured to:

acquire first visual line information of the first user; and perform control of causing the second display device to display the first visual line information of the first user.

10. The information processing system according to claim 1, wherein the at least one processor is configured to:

acquire second visual line information of the second user;

specify, based on the second visual line information, a region of interest to be paid attention, which is a second region of interest to which the second user pays attention in the second visual field image;

acquire, in a case where the region of interest to be paid attention is a predetermined type of region of interest, relevant information related to the region of interest to be paid attention; and perform control of causing the second display device to display the relevant information on the region of interest to be paid attention in a superimposed manner.

11. The information processing system according to claim 1, wherein the at least one processor is configured to:

acquire a first posture image and a second posture image obtained by respectively imaging the first user and the second user in at least one same direction; and perform control of displaying the first posture image and the second posture image on an outside of a region in which the visual field of the second user is displayed on the second display device.

12. The information processing system according to claim 1, wherein the at least one processor is configured to:

acquire a voice of the first user;

convert the voice of the first user into text information; and perform control of causing the second display device to display the text information.

13. The information processing system according to claim 1, wherein the at least one processor is configured to:

generate a second composite image obtained by combining the second visual field image with the information indicating the position of the at least one first region of interest;

generate a first composite image obtained by combining the first visual field image with the information indicating the position of the at least one second region of interest;

perform control of causing the second display device to display the second composite image; and perform control of causing the first display device to display the first composite image.

14. The information processing system according to claim 1, wherein the at least one processor is configured to:

acquire parameter information related to the instrument; and perform control of causing the second display device to display the parameter information.

15. The information processing system according to claim 1, wherein the at least one processor is configured to perform control of causing a third display device viewed by a third user to display the first interest information.

16. The information processing system according to claim 1, wherein the at least one processor is configured to:

acquire a first sub-visual field image showing a visual field of a first sub-user and a second sub-visual field image showing a visual field of a second sub-user;

perform control of causing a second sub-display device viewed by the second sub-user to display information indicating a position of a first sub-region of interest included in the first sub-visual field image; and perform control of causing a first sub-display device viewed by the first sub-user to display information indicating a position of a second sub-region of interest included in the second sub-visual field image.

17. The information processing system according to claim 1, wherein the at least one processor is configured to:

acquire a second sub-visual field image showing a visual field of a second sub-user; and perform control of causing the second display device to display the first interest information and information indicating a position of a second sub-region of interest included in the second sub-visual field image.

18. An information processing method executed by a computer, the information processing method comprising:

acquiring a first visual field image showing a visual field of a first user and a second visual field image showing a visual field of a second user;

performing control of causing a second display device viewed by the second user to display first interest information indicating a position of at least one first region of interest included in the first visual field image; and performing control of causing a first display device viewed by the first user to display second interest information indicating a position of at least one second region of interest included in the second visual field image, wherein the first visual field image and the second visual field image indicate the visual fields of the first user and the second user in a case where the first user and the second user operate the same type of instrument, and wherein each of the at least one first region of interest and the at least one second region of interest is at least one of a portion of a body of the first user or the second user who operates the instrument, at least a part of the instrument, a use target of the instrument, or an edge of the first visual field image or the second visual field image.

19. A non-transitory computer-readable storage medium storing an information processing program causing a computer to execute a process comprising:

acquiring a first visual field image showing a visual field of a first user and a second visual field image showing a visual field of a second user;

performing control of causing a second display device viewed by the second user to display first interest information indicating a position of at least one first region of interest included in the first visual field image; and performing control of causing a first display device viewed by the first user to display second interest information indicating a position of at least one second region of interest included in the second visual field image, wherein the first visual field image and the second visual field image indicate the visual fields of the first user and the second user in a case where the first user and the second user operate the same type of instrument, and wherein each of the at least one first region of interest and the at least one second region of interest is at least one of a portion of a body of the first user or the second user who operates the instrument, at least a part of the instrument, a use target of the instrument, or an edge of the first visual field image or the second visual field image.

* * * * *